United States Patent [19]
Schofield et al.

[11] Patent Number: 6,043,278
[45] Date of Patent: Mar. 28, 2000

[54] PERFLUORALKYL SUBSTITUTED METALLO-BETA-LACTAMASE INHIBITORS

[75] Inventors: Christopher Joseph Schofield; Magnus W Walter; Robert M Adlington; Jack E Baldwin, all of Oxford, United Kingdom; Jean-Marie Frere, Nanotrin, Belgium; Felici Antonio, Verona, Italy

[73] Assignee: Isis Innovation Limited, United Kingdom

[21] Appl. No.: 09/077,333

[22] PCT Filed: Nov. 27, 1996

[86] PCT No.: PCT/GB96/02922

§ 371 Date: Jun. 15, 1998

§ 102(e) Date: Jun. 15, 1998

[87] PCT Pub. No.: WO97/19681

PCT Pub. Date: Jun. 5, 1997

[30] Foreign Application Priority Data

Nov. 28, 1995 [GB] United Kingdom .................. 9524267

[51] Int. Cl.$^7$ ................................................. A61K 31/195
[52] U.S. Cl. ............................... 514/561; 514/2; 514/309
[58] Field of Search ................... 514/2, 561, 309

[56] References Cited

U.S. PATENT DOCUMENTS

| | | | |
|---|---|---|---|
| 2,521,902 | 9/1950 | Coover et al. | 526/248 |
| 5,338,856 | 8/1994 | Ricks et al. | 548/204 |

FOREIGN PATENT DOCUMENTS

| | | |
|---|---|---|
| 0 114 950 | 8/1984 | European Pat. Off. . |
| 0 410 411 | 1/1991 | European Pat. Off. . |
| 0 503 203 | 9/1992 | European Pat. Off. . |
| WO93/25574 | 12/1993 | WIPO . |

OTHER PUBLICATIONS

*Chemical Abstracts*, 124(1), abstract No. 9415a (Jan. 1996).
*Chemical Abstracts*, 122(19), abstract No. 234109g (May 1995).
*Chemical Abstracts*, 121(23), abstract No. 281229k (Dec. 1994).
*Chemical Abstracts*, 113(17), abstract No. 147802y (Oct. 1990).
K. Brady et al., *Biochemistry*, 29(33), 7608–7617 (1990).
K. Brady et al., *Biochemistry*, 29(33), 7600–7607 (1990).
*Chemical Abstracts*, 112(13), abstract No. 11520v (Mar. 1990).
M. Kolb et al., *Liebigs Ann. Chem.*, (1), 1–6 (1990).
N. Peet, *J. Med. Chem.*, 33(1), 394–407 (1990).
M. Kolb et al., *Tetrahedron Lett.*, 27(14), 1579–1582 (1986).
*Chemical Abstracts*, 106(11), abstract No. 85059f (Mar. 1987).
B. Imperiali et al., *Biochemistry*, 25(13), 3760–3767 (1986).
*Chemical Abstracts*, 66(21), abstract No. 95004d (May 1967).
M. Walter et al., *Tetrahedron Lett*, 36(42), 7761–7764 (Oct. 1995).
M. Gilpin et al., *J. Antibiot.*, 48(10), 1081–1085 (1995).
C. Derstine et al., *J. Am. Chem. Soc.*, 118(35), 8485–8486 (1996).
M. Walter et al., *Bioorg. Med. Chem. Lett.*, 6(20), 2455–2458 (1996).

*Primary Examiner*—Kathleen K. Fonda
*Attorney, Agent, or Firm*—Wenderoth, Lind & Ponack, L.L.P.

[57] ABSTRACT

The invention concerns perfluoro-lower-alkyl derivatives of amino acids. A new synthetic route is provided for preparing α-aminotrifluoromethylketones, by converting α-amino acids to oxazolidin-5-ones which are then reacted with Ruppert's Reagent. Fluorinated derivatives of amino acids and peptides are shown to have a new property of inhibiting or inactivating metallo-β-lactamase enzymes, and are thus valuable components of antibacterial formulations. Certain of the trifluoromethyl derivatives of amino acids are new compounds per se.

6 Claims, No Drawings

PERFLUORALKYL SUBSTITUTED METALLO-BETA-LACTAMASE INHIBITORS

This is the U.S. national stage entry under 35 U.S.C. 371 of PCT/GB96/02922, filed Nov. 27, 1996.

This invention concerns perfluoro-lower-alkyl derivatives of amino acids. A new synthetic route is provided for preparing α-aminotrifluoromethylketones. Fluorinated derivatives of amino acids and peptides are shown to have a new property of inhibiting or inactivating certain enzymes. Certain of the trifluoromethyl derivatives of amino acids are new compounds per se.

The catalytic action of a number of proteases is associated with disease processes, e.g. cancer, thrombosis. The inhibition of these protease enzymes is thus of potential therapeutic importance. Trifluoromethylketones including, but not exclusively, trifluoromethylketone derivatives of α-amino acids and peptides are documented inhibitors of proteases in vitro and are currently being developed by the pharmaceutical industry.

β-lactamases are bacterial enzymes which confer resistance to β-lactam antibiotics. They may be divided into four groups on the basis of their primary structure and mechanism [Ambler, R. P., Phil. Trans. R. Soc. Lond. B., 289, 321–331 (1980)]. Classes A, C and D contain a nucleophilic serine residue at their active sites. Class B enzymes do not, but are metalloproteins which require a bivalent transition metal ion (normally zinc) for activity. The class B enzymes are produced by a range of bacteria. Bacteria which produce β-lactamases are able to hydrolyse and thereby inactivate a wide range of β-lactam antibiotics (including those of medicinal and commercial interest, e.g. penicillins, cephalosporins, carbapenems and others). Resistance to β-lactam antibiotics mediated by metallo β-lactamases is becoming an increasing clinical problem [Payne, D., J. Med. Microbiol., 39, 93, 1993.]

The so-called "combination" therapy in which a mixture of a β-lactam antibiotic and an inhibitor of a serine β-lactamase is administered in order to overcome the problem of resistance mediated by the serine β-lactamases, has led to useful and highly effective medications. This approach is exemplified by the pharmaceutical product Augmentin (a Smithkline Beecham product) which is a combination of amoxycillin, an antibiotic and clavulanic acid [Cartwright, S. J. and Coulson, A. F. W., Nature, 278, 360–361 (1979) and references therein.], a β-lactamase inhibitor. To the best of our knowledge there are no literature reports of inhibitors of the class B metallo-β-lactamases, hence a combination therapy approach cannot be used, and thus resistance to them is a particular problem.

This invention is partly based on the discovery that perfluoro-lower-alkyl (i.e. $C_nF_{2n+1}$ where n is 1–4) e.g. trifluoromethyl derivatives of α-amino acids can act as metallo-β-lactamase enzyme inhibitors. Thus, in this aspect the invention provides use of a trifluoromethyl derivative of an amino acid or peptide or a fluorinated β-lactam substrate analogue as a metallo-β-lactamase enzyme inhibitor, or in the preparation of an antibacterial formulation. The invention also provides an antibacterial formulation comprising a mixture of a β-lactam antibiotic and a perfluoro-lower-alkyl derivative of an amino acid or a peptide or a fluorinated β-lactam substrate analogue. A substrate analogue is a compound having a similar shape and binding properties to a β-lactam substrate peptide.

Preferably the perfluoro-lower-alkyl derivative of the amino acid has the formula (I) or (II)

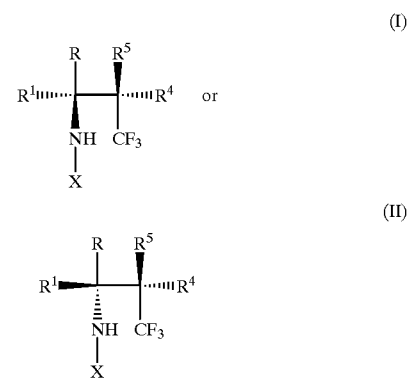

where either $R^4$ is OH and $R^5$ is H, or $C_1-C_{12}$ hydrocarbon; or $R^5$ is OH and $R^4$ is H or $C_1-C_{12}$ hydrocarbon; or each of $R^4$ and $R^5$ is H; or $R^4$ and $R^5$ together are =O, R and $R^1$ are the same or different and each is H or $C_1-C_{12}$ hydrocarbon which is either unsubstituted or which carries an acidic or a basic substituent, X is —COR or —COCH$_2$OR or —COOR or a peptide residue or H including the free base and acid salts thereof.

The hydrocarbon groups R, $R^1$, $R^4$ and $R^5$ may be alkyl, alkenyl, alkynyl, straight chained or branched, cyclic, aromatic, heterocyclic or alicyclic. Examples of acidic and basic substituents include carboxylate, sulphonate, hydroxyl and amine. Preferably one of R and R' is H and the other is a $C_1-C_{12}$ alkyl or aryl or aralkyl group such as methyl or benzyl. Preferably $R^4$ and $R^5$ together are =O.

X may be a protecting group such as tertiary-butoxycarbonyl or benzyloxycarbonyl. Or X may be H or an acid salt of the amine. Or X may be —COR or —COOR or —COCH$_2$OR where R is as defined above. Alternatively, X may be a peptide residue.

Certain of these compounds are believed new per se and form another aspect of this invention. In these new compounds having formula (I) or (II):

R, $R^1$, $R^4$ and $R^5$ are as defined above, and

X is —COCH$_2$OR or —COR, where R is as defined above.

These compounds either have metallo-β-lactamase inhibitor properties or are intermediates in the production of such compounds.

The following experimental section demonstrates the activity of certain α-amino trifluoromethyl derivatives as inhibitors against four different metallo-β-lactamases. The eight compounds tested have been given the numbers 2 to 9, and their activities compared with a known compound 1 having the formula PhCOCH$_2$COCF$_3$.

The structures of compounds 2 to 9 are set out in the following table with reference to structures (I) and (11) above:

| Compound | Structure | R, $R^1$ | $R^4$, $R^5$ | X |
|---|---|---|---|---|
| 2 | (II) | PhCH$_2$—, H | =O | —COCH$_2$OPh |
| 3 | (I) | PhCH$_2$—, H | =O | —COCH$_2$OPh |
| 4 | (I) | PhCH$_2$—, H | OH, H | —COCH$_2$OPh |
| 5 | (II) | PhCH$_2$—, H | OH, H | —COCH$_2$OPh |

-continued

| Compound | Structure | R, R¹ | R⁴, R⁵ | X |
|---|---|---|---|---|
| 6 | (I) | CH₃, H | =O | —COCH₂OPh |
| 7 | (II) | CH₃, H | =O | —COCH₂OPh |
| 8 | (I) | CH₃, H | OH, H | —COCH₂OPh |
| 9 | (II) | CH₃, H | OH, H | —COCH₂OPh |

Synthesis of N-phenoxyacetyl α-amino trifluoromethylketones

Some of the compounds which were found to be active against metallo β-lactamases were obtained according to the general scheme below which is based on a known literature procedure (reference: Skiles, J. W. et al, J. Med. Chem. 1992, 35, 641–662), and some by the novel procedure described in a later section.

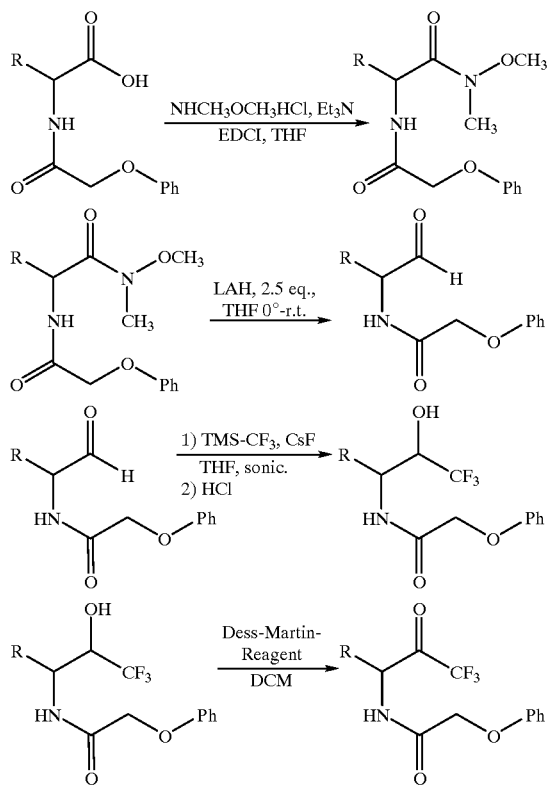

Assay Conditions

Class B β-lactamases were purified according to published[4] or standard procedures from a range of bacteria, including: *Xanthomonas maltophilia, Bacillus cereus, Pseudomonas aeruginosa* and *Aeromonas hydrophila.*

Assays for inhibition were also carried out according to published procedures[4]. Kinetic experiments were typically carried out at 30° C. with 30 mM sodium cacodylate buffer, pH 6.5, containing 0.1 mM ZnCl₂.

The $K_i$ (inhibition constant) values were determined by analysing the initial rate of hydrolysis at different inhibitor concentrations using the following reporter substrates: 30 μm nitrocefin (*X. maltophilia* enzyme), 200 μM imipenem (*A. hydrophila*), or 1 mM cephalosporin C (*B. cereus* and *P. aeruginosa* enzymes). Data analysis was carried out according to standard kinetic procedures [Felici, A. et al., Biochem. J., 291, 151–155 (1993) and references therein].

The following are exemplary kinetic data which illustrate the use of trifluoromethylketone derivatives for the inhibition of metallo β-lactamases. The data indicate that inhibition may be characterised as occurring via either a competitive process and/or by a process resulting in inactivation of the enzymes or by another as yet unspecified process.

Compounds 3, 6, 7 and 9 behaved as competitive inhibitors of the *X. maltophilia* enzyme with $K_i$ values of 15 μM, 1.5 μM, 3.0 μM and 35 μM, respectively.

Compounds 2, 3, 4, 5, 6, 7, 8, 9 and 1 were similarly shown to be competitive inhibitors of the *B. cereus* enzyme with $K_i$ values of 1 mM, 500 μM, 1 mM, 30 μM, 30 μM, 700 μM, 300 μM, 700 μM and 300 μM, respectively.

Compounds 3, 4, 5, 6, 7, 8 and 9 were similarly shown to be competitive inhibitors of the *P. aeruginosa* enzyme with $K_i$ values of 530 μM, 900 μM, 60 μM, 300 μM, 500 μM, 400 μM, and 400 μM, respectively.

Compounds 3, 4, 5, 6, 7 and 9 were also shown to be inhibitors of the *A. hydrophila* enzyme. Further kinetic analyses showed them to act as inactivators (no reactivation was observed) of the A. hydrophila enzyme. The following kinetic parameters were obtained, where K=apparent binding constant between the enzyme and substrate and $k_{+2}$= apparent rate constant for inactivation as in the following scheme:

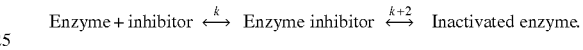

Kinetic data for compound 3: K=6 μM, $k_{+2}=4.3\times10^{-2}s^{-1}$
for compound 4: K=19 μM, $k_{+2}=4.3\times10^{-2}s^{-1}$
for compound 5: K=20 μM, $k_{+2}=3.9\times10^{-2}s^{-1}$
for compound 6: K=44 μM, $k_{+2}=4.0\times10^{-2}s^{-1}$
for compound 7: K=11 μM, $k_{+2}=11\times10^{-2}s^{-1}$
for compound 9: K=217 μM, $k_{+2}=1.1\times10^{-2}s^{-1}$ Another aspect of the invention concerns a novel synthesis of N-substituted and peptidic α-amino trifluoromethylketones. Thus the invention provides a method of making a trifluoromethylketone from a corresponding starting optionally N-protected α-amino acid, comprising the steps:

a) converting the starting α-amino acid to a corresponding oxazolidin-5-one.
b) reacting the oxazolidin-5-one with a trifluoromethyl trialkylsilane to form a C-2 substituted oxazolidine.
c) effecting desilylation and ring-cleavage of the C-2 substituted oxazolid in-5-one.

Preferably the steps are performed according to the reaction scheme:

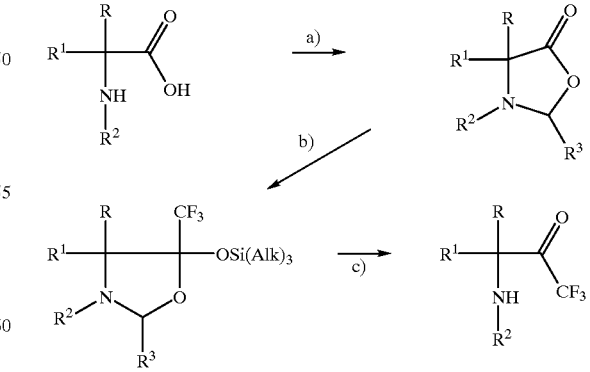

where R² is a protecting group

R and R¹ are the same or different and each is H or $C_1$–$C_{12}$ hydrocarbon which is either unsubstituted or which carries an acidic or a basic substituent, and $R^3$ is H or $C_1$–$C_{12}$ hydrocarbon which is either unsubstituted or which carries a hydroxy or alkoxy substituent.

Various synthetic approaches to this class of compounds have been reported including a modified Dakin-West procedure, reaction of trifluoroacetic anhydride with ketenes, and trifluoromethyl carbanions[1]. The latter approach is, however, of limited utility due to the well-documented tendency of the trifluoromethyl anion to undergo fluoride elimination. Ruppert and coworkers[2] have developed a stable trifluoromethyl anion equivalent in the form of (trifluoromethyl)trimethylsilane (Ruppert's Reagent/TMS-$CF_3$), which is an efficient nucleophilic trifluoromethylation agent for addition to certain carbonyl compounds[3]. Fluoride-catalysed addition reaction of TMS-$CF_3$ to ketones or aldehydes generally proceeds in good yields, but efficient reaction with carboxylic acid derivatives has only been reported in the case of five- and six-membered lactones[3].

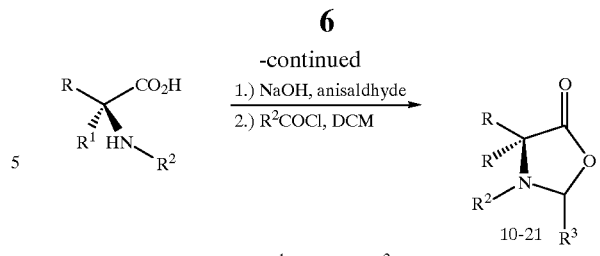

R = amino acid side chain; $R^1 = CH_3$, H; $R^2 = PhCH_2O$, PhCO;
$R^3$ = para-$H_3COC_6H_4$, tert-butyl.

The addition of Ruppert's Reagent to oxazolidin-5-ones occurs in very good to excellent yields and tolerates a wide variety of amino acid side-chains (see Table 1). Also x-disubstituted oxazolidin-5-ones react in very good yields (19, 20 in Table 1).

TABLE 1

| Entry | Nr. | R | $R^1$ | $R^2$ | $R^3$ | method | yield | TFMK |
|---|---|---|---|---|---|---|---|---|
| I | 1 | $PhCH_2$ | H | BOC | H | A | 1a: 98% | — |
| II | 2 | $H_3C$ | H | BOC | H | A | 2a: 85% | — |
| III | 3 | $(H_3C)_2CH$ | H | BOC | H | A | 3a: 84% | — |
| IV | 4 | $(H_3C)CH_2C$ | H | BOC | H | A | 4a: 95% | — |
| V | 5 | $PhCH_2SCH_2$ | H | BOC | H | A | 5a: 77% | — |
| VI | 6 | $PhCH_2$ | H | CBZ | H | A | 6a: 95% | — |
| VII | 7 | $H_3C$ | H | CBZ | H | A | 7a: 69% | — |
| VIII | 8 | $MeO_2CCH_2$ | H | CBZ | H | AS | 8a: 50% | — |
| IX | 9 | $MeO_2C(CH_2)_2$ | H | CBZ | H | A | 9a: 73% | — |
| X | 10 | $PhCH_2$ | H | CBZ | t-Bu | A | 10a: 80% | — |
| XI | 11 | $H_3C$ | H | CBZ | t-Bu | A | 11a: 38% | — |
| XII | 12 | $PhCH_2$ | H | CBZ | Ph | A | 12a: 53% | — |
| XIII | 13 | $PhCH_2$ | H | CBZ | $\pi$-$H_3COC_6H_4$ | B | 13a: 91% | 13c |
| XIV | 14 | $H_3C$ | H | CBZ | $\pi$-$H_3COC_6H_4$ | B | 15a: 92% | 14c |
| XV | 15 | $(H_3C)CH_2CH_2$ | H | CBZ | $\pi$-$H_3COC_6H_4$ | B | 15a: 85% | 15c |
| XVI | 16 | $PhCH_2$ | H | PhCO | t-Bu | B | 16a: 71% | 16c |
| XVII | 17 | $H_3C$ | H | PhCO | $\pi$-$H_3COC_6H_4$ | B | 17a: 94% | 17c |
| XVIII | 18 | $H_3C$ | H | $PhOCH_2CO$ | $\pi$-$H_3COC_6H_4$ | B | 18a: 85% | 18c |
| XIX | 19 | $H_3C$ | $H_3C$ | PhCO | $\pi$-$H_3COC_6H_4$ | B | 19a: 72% | 19c |
| XX | 20 | $H_3C$ | $H_3C$ | $PHOCH_2CO$ | $\pi$-$H_3COC_6H_4$ | B | 20a: 75% | 20c |
| XXI | 21 | H | H | PhCO | $\pi$-$H_3COC_6H_4$ | B | 21a: 75% | 21c |
| XXII | 22 | $(H_3C)_2CH$ | H | CBZ | $\pi$-$H_3COC_6H_4$ | B | 22a: 81% | 22c |

The present inventors have studied the reaction of TMS-$CF_3$ with oxazolidin-5-ones[4] derived from both natural and unnatural amino acids, and developed a new general route to trifluoromethyl ketone derivatives of amino acids. α-Amino acids can be readily converted into oxazolidin-5-ones by known literature methods[5,6] (Scheme 1).

In the case of paraformaldehyde derived oxazolidin-5-ones CsF with sonication was used as a fluoride source (method A in Scheme 2), whereas for C-2 substituted oxazolidin-5-ones a commercial solution of tetrabutylammonium fluoride in THF was preferable (method B in Scheme 2). The silylated adducts 1a–22a were desilylated in quantitative yield using 1 equivalent of a solution of tetrabutylammonium fluoride in THF or 1 equivalent of CsF with sonication.

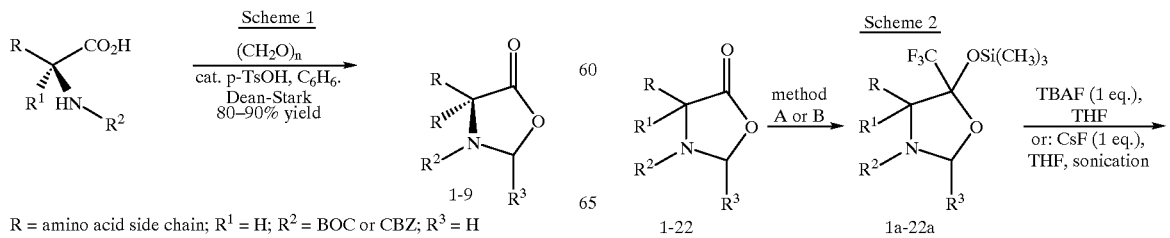

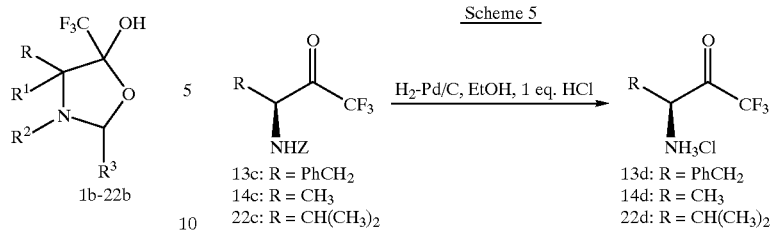

Oxazolidin-5-ones having a para-methoxyphenyl or a tert-butyl substituent at the C-2 position were cleaved by stirring in acetonitrile at 40–50° C. in the presence of strongly acidic ion exchange resin for 48 to 72 hours. Oxazolidin-5-one 16a with a C-2 tert-butyl substituent and a benzoyl group at the nitrogen was also hydrolysed under similar conditions. The product N-substituted α-amino-trifluoromethyl ketones were obtained in excellent yields (Scheme 3).

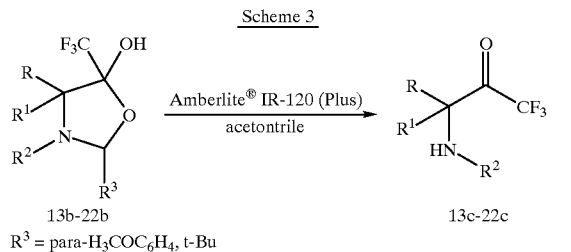

Analytical data of 13c obtained via addition of Ruppert's Reagent to the oxazolidin-5-one 13 followed by hydrolysis were the same as those obtained for the synthesis of 13c via a known route (Scheme 4) starting from N-benzyloxycarbonyl-(L)-phenylalaninal, ($[\alpha]_D^{20}$=+23.2° (c=CHCl$_3$) for 13c prepared as in Scheme 3, and $[\alpha]_D^{20}$=+ 22.9° (c=0.5, CHCl$_3$) for 13c prepared as in Scheme 4).

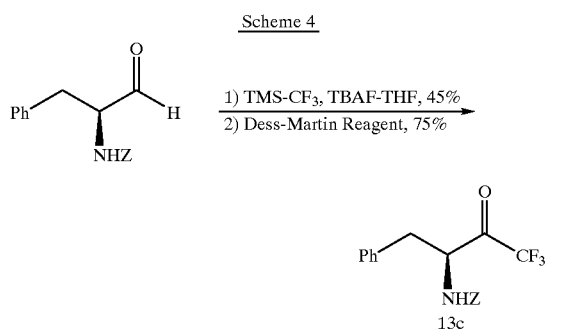

Z is CBZ (benzyloxycarbonyl)

N-substituted α-amino trifluoromethyl ketones are stable highly crystalline compounds which can be stored for long periods without any sign of decomposition.

Compounds 13c and 14c were converted into hydrochloride salts of the corresponding α-amino trifluoromethyl ketones in quantitative yield using a standard hydrogenation procedure (Scheme 5).

To the best of our knowledge hydrochloride salts of α-amino trifluoromethyl ketones have not yet been described in the literature. Such compounds are new per se and form another aspect of this invention. First studies have shown that hydrochloride salts of α-amino trifluoromethyl ketones undergo the same reactions as the well known hydrochloride salts of α-amino acids. Thus, the N atom in 13d was derivatised as the benzoyl amide. Coupling with activated amino acid derivatives provided access to peptidic trifluoromethyl ketones (Scheme 6).

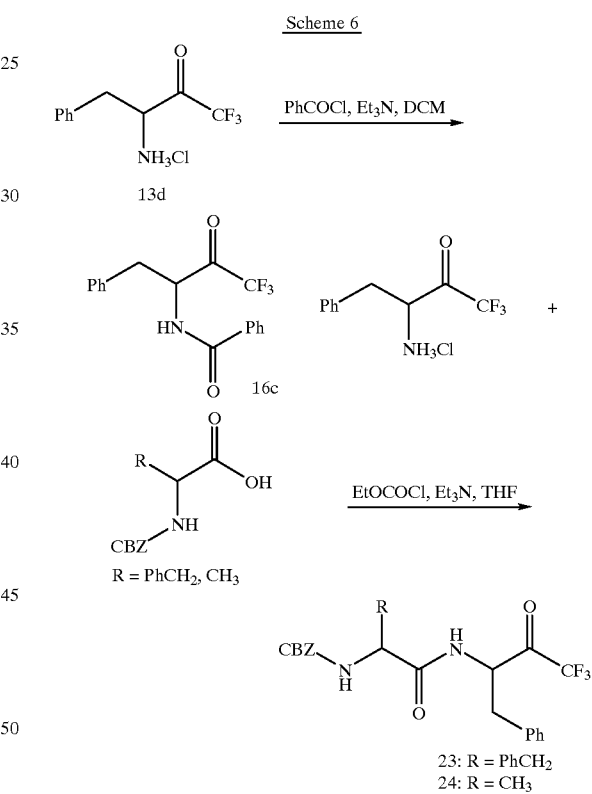

Using amino acid fluorides as acylating reagents[9,10] peptidic trifluoromethyl ketones were obtained as single diastereomers from optically pure trifluoromethyl ketone hydrochloride salts (Scheme 7).

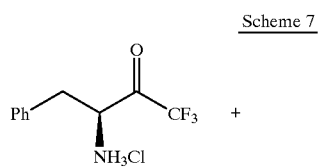

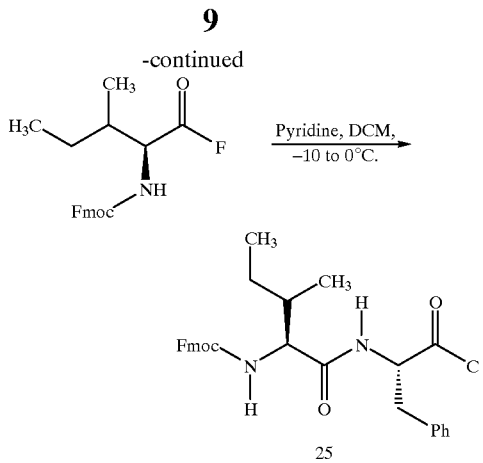

The present invention allows the facile synthesis of a very large number of peptidic α-amino trifluoromethyl ketones which are known to be very potent protease inhibitors and therefore of great biological interest.

EXPERIMENTAL SECTION

Melting points are uncorrected. $^1$H, $^{19}$F, and $^{13}$C NMR spectra were recorded at the indicated field strengths. $^{19}$F NMR spectra were referenced externally to $CFCl_3$ at 0.00 ppm. Elemental analyses were performed at the Dyson Perrins Laboratory, University of Oxford. High resolution mass spectra were obtained by the EPSRC mass spectrometry service, Swansea. All separations were effected under flash chromatography conditions using either Acros C60 (0.035–0.07 mm) silica gel or Sigma-Aldrich octadecyl modified silica gel (40–63, 550 m$^2$g, 60 Å) following a literature procedure for reversed phase column chromatography[ref]. Sonication was carried out in a Kerry Pulsatron. Amberlite® IR 120 (Plus) ion exchange resin was obtained from Aldrich and 'activated' by refluxing in 2M hydrochloric acid and washed several times with water before use. All reagents were obtained from commercial suppliers and used as received unless otherwise stated. THF was distilled from potassium/benzophenone ketyl under a nitrogen atmosphere. DCM was distilled from calcium hydride under a nitrogen atmosphere.

General procedure A: Preparation of N-CBZ and N-BOC protected oxazolidin-5-ones: A mixture of N-CBZ or N-BOC-protected amino acid (10.0 mM), para-formaldehyde (400 mg), and para-toluenesulfonic acid (100 mg) in benzene (150 ml) was refluxed for 1 h, the water being distilled off and collected in a water separator as it was formed (Dean-Stark-conditions). The benzene solution was allowed to cool to room temperature and washed with aqueous sodium bicarbonate solution (50 mL) and brine (50 mL). After drying over magnesium sulphate and evaporation of solvents in vacuo, the crude product was purified by column chromatography or by crystallisation from suitable solvents.

General procedure B: Formation of Schiff-base salts of amino acids: The amino acid (10.0 mM) was dissolved in a 1M solution of sodium hydroxide (10 mL). Gentle warming or addition of ethanol was sometimes required to effect solution. The solution was then reduced in vacuo until solid began to appear at which time one molar equivalent of aldehyde was added. Concentration in vacuo was continued until the reaction mixture solidified. The solid was suspended in diethyl ether (150 mL), filtered and washed thoroughly with same solvent and dried in vacuo. This procedure afforded the Schiff-base salts in nearly quantitative yield. The infrared spectrum exhibited the characteristic absorption peaks at 1665 and 1800–1810 cm$^{-1}$.

General procedure C: Preparation of N-CBZ protected, C-2 substituted oxazolidin-5-ones: To a suspension of carefully ground Schiff-base salt (10.0 mM) in DCM (150 mL) was added benzyl chloroformate (1.43 mL, 10.0 mM) over a period of 6 h at −15° C. under an argon atmosphere. The resulting mixture was stirred at −15° C. for 72 h after which time the reaction mixture was reduced in vacuo and ethyl acetate (100 mL) was added. The organic layer was washed with aqueous hydrochloric acid (50 mL), saturated sodium bicarbonate solution (50 mL) and brine (50 mL). After re-extraction of the aqueous layer with ethyl acetate (50 mL) the combined organic layers were washed with brine (2×75 mL) and dried over magnesium sulphate. The solvents were removed in vacuo and the products purified by column chromatography or by crystallisation from suitable solvents.

General procedure D: Preparation of N-amide protected, C-2 substituted oxazolidin-5-ones: A mixture of carefully ground Schiff base salt (10 mM) and the appropriate acid chloride (10 mM) in DCM (150 mL) was refluxed for 12 h under an argon atmosphere. The reaction mixture was reduced in vacuo and ethyl acetate (100 mL) was added. The organic layer was washed with aqueous hydrochloric acid (50 mL), saturated sodium bicarbonate solution (50 mL) and brine (50 mL). After re-extraction of the aqueous layer with ethyl acetate (50 mL) the combined organic layers were washed with brine (2×75 mL) and dried over magnesium sulphate. The solvents were removed in vacuo and the products purified by column chromatography or by crystallisation from suitable solvents.

General procedure E (Method A in Table 1): To a solution of oxazolidin-5-one (1 mM) in dry THF (5 mL) were added caesium fluoride (catalytic amounts) and (trifluoromethyl)-trimethylsilane (0.19 mL, 1.20 mM, 1.20 eq) under an argon atmosphere. The flask was placed in a sonicator and the reaction followed by TLC analysis. After all starting material had been consumed (usually 20 to 60 min) the mixture was diluted with ethyl acetate (10 mL), washed with water (10 mL), brine (10 mL), and dried over magnesium sulphate. The solvents were removed in vacuo and the products purified by flash column chromatography.

General procedure F (Method B in Table 1): To a solution of oxazolidin-5-one (1.00 mM) in dry THF (5 mL) were added (trifluoromethyl)trimethylsilane (0.19 mL, 1.20 mM, 1.20 eq). and tetrabutylammonium fluoride (25 μL of a 1.00 M solution in THF, 0.025 mM) under an argon atmosphere at room temperature resulting in a yellow solution. The reaction was followed by TLC analysis. After all starting material had been consumed the mixture was taken up in ethyl acetate (10 mL), washed with water (2×10 mL), brine (10 mL), and dried over magnesium sulphate. The solvents were removed in vacuo and the products purified by flash column chromatography.

General procedure G: Desilylation of adducts 1a–21a: To a solution of silylated adduct (1.00 mM) in THF (5 mL) was added tetrabutylammonium fluoride (1.20 mL of a 1.00 M solution in THF, 1.20 eq). The reaction was followed by TLC analysis. After all starting material had been consumed, ethyl acetate (10 mL) and aqueous hydrochloric acid (10 mL) were added. The organic layer was separated and washed with saturated sodium bicarbonate solution (10 mL) and brine (10 mL). The combined organic phases were dried over magnesium sulphate and the solvents evaporated in vacuo.

General procedure H: Hydrolysis of 5-hydroxy-5-trifluoromethyloxazolidins: To a solution of 5-hydroxy-5-trifluoromethyloxazolidin (1 mM) in acetonitrile (15 mL) was added strongly acidic cation exchange resin (2.0 g) and stirred at 45° C. until all starting material had disappeared by TLC (usually 36–48 h) after which time a deeply red solution was obtained. The crude product was diluted with acetonitrile (25 mL), filtered through Celite® and the resin thoroughly washed with acetonitrile. After removal of the solvent in vacuo, the residue was taken up in ethyl acetate (25 mL) and washed with saturated sodium bicarbonate solution (15 mL) and brine (15 mL). After drying over magnesium sulphate the solvent was removed in vacuo. Purification was achieved by reversed phase column chromatography on octadecylsilyl coated silica gel.

(4S)-4-Benzyl-N-tert-butyloxycarbonyl-1,3-oxazolidin-5-one (1) was prepared from N-tert-butyloxycarbonyl-(L)-phenylalanine (2.65 g, 10.0 mM) and para-toluene-sulfonic acid (30 mg) following general procedure A and obtained as a white solid after crystallisation from diethyl ether (1.49 g, 54%): $[\alpha]_D^{20}$+23.5 (c 1.0, $CHCl_3$); mp 84–86° C.; IR (KBr): 1795, 1705 $cm^{-1}$; $^1H$ NMR (500 MHz, $d_8$-toluene, 90° C.): δ 6.97–7.08 (m, 5H), 4.75 (d, J=4 Hz, 1H), 4.03–4.05 (m, 2H), 3.17 (dd, J=4, 14 Hz, 1H), 2.92 (dd, J=3, 14 Hz, 1H), 1.31 (s, 9H); $^{13}C$ NMR (50.3 MHz, $CDCl_3$): δ 172.7, 153.2, 135.0, 129.8, 128.9, 127.6, 82.0, 78.0, 56.3, 34.3, 28.6; LRMS ($NH_3$): 295 ($MNH_4^+$). Anal. Calcd for $C_{15}H_{19}NO_4$: C, 64.96; H, 6.90; N, 5.05; found: C, 64.93; H, 6.73; N, 4.83.

(4S)-N-tert-Butyloxycarbonyl4-methyl-1,3-oxazolidin-5-one (2) was prepared from N-tert-butyloxycarbonyl-(L)-alanine (1.89 g, 10.0 mM) and para-toluenesulfonic acid (30 mg) following general procedure A and obtained as fine white needles after crystallisation from chloroform (1.49 g, 74%): $[\alpha]_D^{20}$+78.1 (c 1, $CHCl_3$); mp 64–67° C.; IR (KBr) 1795, 1705 $cm^{-1}$; $^1H$ NMR (200 MHz, $CDCl_3$): δ 5.40 (d, J=2 Hz, 1H), 5.20 (d, J=2 Hz, 1H), 4.50 (q, J=7 Hz, 1H), 1.55 (d, J=7 Hz, 3H), 1.45 s (s, 9H); $^{13}C$ NMR (50.3 MHz, $CDCl_3$): δ 173.5, 152.0, 81.4, 77.3, 50.3, 27.8, 16.3; LRMS ($NH_3$): 219 ($MNH_4^+$). Anal. Calcd for $C_9H_{15}NO_4$: C, 53.72; H, 7.51; N, 6.96; found: C, 53.58; H, 7.71; N, 6.70.

($^4$S)-N-tert-Butyloxycarbonyl4-isopropyl-1,3-oxazolidin-5-one (3) was prepared from N-tert-butyloxycarbonyl-(L)-valine (2.17 g, 10.0 mM) and para-toluenesulfonic acid (30 mg) following general procedure A and obtained as a white solid after crystallisation from chloroform (1.67 g, 73%): $[a]_D^{20}$ +104.9 (c 1, $CHCl_3$); mp 43–45° C.; IR (KBr): 1795, 1705 $cm^{-1}$; $^1H$ NMR (200 MHz, $CDCl_3$): 67 5.55 (br, 1H), 5.10 (d, J=4 Hz, 1H), 4.15 (d, J=4 Hz, 1H), 2.21–2.43 (m, 1H), 1.49 (s, 9H), 1.06 (d, J=7 Hz, 3H), 1.02 (d, J=7 Hz, 3H); $^{13}C$ NMR (50.3 MHz, $CDCl_3$): d 171.8, 152.6, 81.6, 78.4, 59.9, 31.1, 27.9, 17.9, 17.5; LRMS ($NH_3$): 230 ($MH^+$). Anal. Calcd for $C_{11}H_{19}NO_4$: C, 57.63; H, 8.35; N, 6.11; found: C, 57.62; H, 8.54; N, 5.93.

(4S)-N-tert-Butyloxycarbonyl 4-isobutyl-1,3-oxazolidin-5-one (4) was prepared from N-tert-butyloxycarbonyl-(L)-leucine (2.31 g, 10.0 mM) and para-toluenesulfonic acid (30 mg) following general procedure A and obtained as a colourless, slowly solidifying oil after purification by flash column chromatography, using 30% chloroform/petroleum ether as eluant (1.91 g, 79%): $[\alpha]_D^{20}$+88.5 (c 0.9, $CHCl_3$); IR ($CHCl_3$): 1790, 1720 $cm^{-1}$; $^1H$ NMR (200 MHz, $CDCl_3$): δ 5.48 (d, J=5 Hz, 1H), 5.09 (d, J=5 Hz, 1H), 4.22 (t, J=6 Hz, 1H), 1.43 (s, 9H), 1.23–1.16 (m, 3H), 0.92 (d, J=5 Hz, 3H), 0.90 (d, J=5 Hz, 3H); $^{13}C$ NMR (50.3 MHz, $CDCl_3$): δ 172.9, 152.2, 81.5, 77.8, 53.2, 39.4, 27.9, 24.2, 22.4, 22.2; LRMS ($NH_3$): 244 ($MH^+$).

(4R)-4-(S-Benzylthiomethyl)-N-tert-butyloxycarbonyl-1,3-oxazolidin-5-one (5) was prepared from S-benzylthiomethyl-N-tert-butyloxycarbonyl-(L)-cysteine (3.11 g, 10.0 mM) and para-toluenesulfonic acid (30 mg) following general procedure A and obtained as fine white needles after crystallisation from diethyl ether (1.68 g, 52%): $[\alpha]_D^{20}$+140.0 (c 1.0, $CHCl_3$); mp 63–65° C.; IR (KBr): 1800, 1700 $cm^{-1}$; $^1H$ NMR (500 MHz, $d_8$-toluene, 90° C.): 67 6.81–7.34 (m, 5H), 4.96 (br, d, J=4 Hz, 1H), 4.93 (dd, J=1, 4 Hz, 1H), 3.95 (dd, J=3, 4 Hz, 1H), 3.52 (d, J=13 Hz, 1H), 3.49 (d, J=13 Hz, 1H), 3.03 (dd, J=4, 14 Hz, 1H), 2.71 (dd, J=3, 14 Hz, 1H), 1.29 (s, 9H); $^{13}C$ NMR (50.3 MHz, $CDCl_3$): δ 171.8, 152.4, 137.6, 129.0, 128.6, 127.3, 82.2, 78.9, 56.4, 37.4, 37.3, 28.3; LRMS (EI): 324 ($MH^+$). Anal. Calcd for $C_{16}H_{21}NO_4S$: C, 59.42; H, 6.55; N, 4.33; found: C, 59.25; H, 6.40; N, 4.25.

(4S)-N-Benzyloxycarbonyl4-methoxycarbonylmethyl-1,3-oxazolidin-5-one (8): To a solution of (4S)-3-benzyloxycarbonyl-4-carboxymethyl-1,3-oxazolidin-5-one[11] (1.00 g, 3.58 mM) in ethyl acetate (25 mL) was added a solution of diazomethane (10.0 mM) in diethyl ether (45 mL) over 25 min. Excess diazomethane was removed by addition of a few drops of acetic acid. The organic layer was then washed with aqueous sodium bicarbonate solution (3×50 mL) and brine (50 mL). After drying over magnesium sulphate and removal of solvents in vacuo (6) was obtained as a colourless solid from diethyl ether (1.01 g, 96%): $[\alpha]_D^{20}$+84.0 (c 2, $CHCl_3$); mp 90–93° C.; IR (KBr): 1805, 1735 $cm^{-1}$; $^1H$ NMR (500 MHz, $d_8$-toluene): δ 6.80–7.11 (m, 5H), 4.99 (dd, J=1, 4 Hz, 1H), 4.95 (d, J=4 Hz, 1H), 4.92 (d, J=12 Hz, 1H), 4.85 (d, J=12 Hz, 1H), 3.81 (dd, J=3.5, 4.5 Hz, 1H), 3.20 (s, 3H), 2.90 (dd, J=4.5, 7 Hz, 1H), 2.60 (dd, J=3.5, 7 Hz, 1H); $^{13}C$ NMR (50.3 MHz, $CDCl_3$): δ 172.8, 170.1, 152.6, 135.4, 128.7, 128.5, 128.2, 78.4, 67.8, 52.7, 51.5, 34.0; LRMS ($NH_3$): 294 ($MH^+$). Anal. Calcd for $C_{14}H_{15}NO_6$: C, 57.33; H, 5.15; N, 4.76; found: C, 57.15; H, 5.04; N, 4.71.

(4S)-N-Benzyloxycarbonyl-4-methoxycarbonylethyl-1,3-oxazolidin-5-one (9): To a solution of (4S)-3-benzyloxycarbonyl4-carboxyethyl-1,3-oxazolidin-5-one[ref] (1.0 g, 3.41 mM) in ethyl acetate (25 mL) was added a solution of diazomethane (10.0 mM) in diethyl ether (45 mL) over 25 min. Excess diazomethane was removed by addition of a few drops of acetic acid. The organic layer was then washed with aqueous sodium bicarbonate solution (3×50 mL) and brine (50 mL). After drying over magnesium sulphate and removal of solvents in vacuo (8) was obtained as a colourless solid from diethyl ether (1.02 g, 97%): $[\alpha]_D^{20}$+83.1 (c 2, $CHCl_3$); mp 96–97° C.; IR ($CHCl_3$): 1805, 1735 $cm^{-1}$; $^1H$ NMR (200 MHz, $CDCl_3$): δ 7.38–7.49 (m, 5H), 5.54 (br, 1H), 5.23–5.47 (m, 3H), 4.45 (dd, J=4 Hz, 1H), 3.61 (s, 3H), 2.01–2.46 (m, 4H); $^{13}C$ NMR (50.3 MHz, $CDCl_3$): δ 172.5, 171.8, 153.0, 135.3, 128.7, 128.6, 128.3, 77.8, 68.1, 54.0, 51.8, 29.1, 25.9; LRMS ($NH_3$): 325 ($MNH_4+$); HRMS: calcd for $C_{15}H_{18}NO_6$ ($MH^+$): 308.1134; found: 308.1134.

(2S,4S)-4-Benzyl-N-benzyloxycarbonyl-2-tert-butyl-1,3-oxazolidin-5-one (10) was prepared from sodium N-(tert-butylidene)-(L)-phenylalaninate (2.55 g, 10.0 mM) and benzyl chloroformate (1.43 mL, 10.0 mM) following general procedure C and obtained as a colourless oil, after purification by flash column chromatography, using 25% diethyl ether/petrol as eluant (2.08 g, 57%, single diastereomer): $[\alpha]_D^\circ$-3.0 (c 1.0, $CHCl_3$); IR ($CHCl_3$): 1795, 1725 $cm^{-1}$; $^1H$ NMR (200 MHz, $CDCl_3$): δ 7.26–7.43 (m, 10H), 5.59 (s, 1H), 5.17 (d, J=12 Hz, 1H), 4.95 (d, J=12 Hz, 1H), 4.51 (dd, J=6, 7 Hz, 1H), 3.25 (dd, J=7, 12 Hz, 1H), 3.15 (dd, J=6, 12 Hz, 1H), 1.04 (s, 9H); $^{13}C$ NMR: δ 171.9, 155.8, 136.7, 135.1, 129.4, 128.9, 126.9, 128.5, 128.4, 96.1, 68.2, 58.8, 39.2, 36.9, 24.8; LRMS (NH$_3$): 385 (MNH$_4^+$); HRMS: calcd for C$_{22}$H$_{26}$NO$_4$ (MH$^+$): 368.1862; found: 368.1862.

(2S,4S)-N-Benzyloxycarbonyl-2-tert-butyl-4-methyl-1,3-oxazolidin-5-one (11) was prepared from sodiumN-(tert-butylidene)-(L)-alaninate[8] (1.79 g, 10.0 mM) and benzyl chloroformate (1.42 mL, 10.0mM) following general procedure C and obtained as a colourless oil after purification by flash column chromatography, using 16% diethyl ether/petrol as eluant (1.39 g, 48%, mixture of 2 diastereomers in a ratio of 2:1 by $^1$H NMR): IR (CHCl$_3$): 1800, 1720 cm$^{-1}$; $^1$H NMR (200 MHz, CDCl$_3$): δ 7.32–7.43 (5H, m), 5.66 (s, 1H, minor diastereomer), 5.55 (s, 1H, major io diastereomer), 5.16–5.20 (m, 2H), 4.37 (q, J=6 Hz, 1H, minor diastereomer), 4.12 (q, J=7 Hz, 1H, major diastereomer), 1.61 (d, J=6 Hz, 3H, minor diastereomer), 1.54 (d, J=7 Hz, 3H, major diastereomer), 0.96 (s, 9H, minor diastereomer), 0.93 (s, 9H, major diastereomer); $^{13}$C NMR (50.3 MHz, CDCl$_3$): δ 173.8, 173.1, 155.7, 135.3, 128.6, 128.2, 96.2, 94.9, 68.0, 67.7, 53.4, 53.0, 39.4, 37.1, 24.8, 24.6, 17.4; LRMS (NH$_3$): 309 (MNH$_4^+$); HRMS: calcd for C$_{16}$H$_{22}$NO$_4$ (MH$^+$): 292.1549; found: 292.1549.

(2S,4S)-4-Benzyl-N-benzyloxycarbonyl-2-(4'-methoxyphenyl)-1,3-oxazolidin-5-one (13) was prepared from sodium N-(para-methoxybenzylidene)-(L)-phenylalaninate (3.05 g, 10.0 mM) and benzyl chloroformate (1.43 mL, 10.0 mM) following general procedure C and obtained as a white solid after crystallisation from diethyl ether (2.87 g, 69%): [α]$_D^{20}$+50.1 (c 1.0, CHCl$_3$); mp 85° C.; IR (KBr): 1795, 1700 cm$^{-1}$; $^1$H NMR (500 MHz, d$_8$-toluene, 90° C.): δ 6.49–7.08 (m, 14H), 6.04 (s, 1H), 4.92 (d, J=12 Hz, 1H), 4.83 (d, J=12 Hz, 1H), 4.19 (dd, J=4, 6 Hz, 1H), 3.39 (s, 3H), 3.25 (dd, J=6, 14 Hz, 1H), 3.08 (dd, J=4, 14 Hz, 1H); $^{13}$C NMR (50.3 MHz, CDCl$_3$): δ 171.4, 160.3, 151.5, 135.3, 129.2, 128.8, 128.5, 128.2, 127.3, 113.4, 89.3, 67.8, 58.4, 55.3, 34.5; LRMS (EI): 418 (MH$^+$). Anal. Calcd for C$_{25}$H$_{23}$NO$_5$: C, 71.93; H, 5.55; N, 3.35. Found: C, 72.22; H, 5.36; N, 3.28.

(2S,4S)-N-Benzyloxycarbonyl-2-(4'-methoxyphenyl)-4-methyl-1,3-oxazolidin-5-one (14) was prepared from sodium N-(para-methoxybenzylidene)-(L)-alaninate (2.29 g, 10.0 mM) and benzyl chloroformate (1.43 mL, 10.0 mM) following general procedure C and obtained as a white solid after purification by flash column chromatography, using 33% ethyl acetate/petrol as eluant (1.75g, 51%, single diastereomer): [α]$_D^{20}$+99.9 (c 1.0, CHCl$_3$); mp 97–99° C.; IR (KBr): 1790, 1695 cm$^{-1}$; $^1$H NMR (500 MHz, d$_8$-toluene, 90° C.): δ 6.56–7.06 (m, 9H), 6.11 (s, 1H), 4.82 (d, J=12 Hz, 1H), 4.72 (d, J=12 Hz, 1H), 4.13 (q, J=7 Hz, 1H), 3.35 (s, 3H), 1.47 (d, J=7 Hz, 3H); $^{13}$C NMR (50.3 MHz, CDCl$_3$): δ 172.3, 160.8, 152.0, 135.2, 128.4, 128.0, 127.7, 125.8, 121.3, 114.1, 89.2, 67.5, 55.3, 52.1, 16.5; LRMS (NH$_3$): 342 (MNH$_4^+$). Anal. Calcd for C$_{19}$H$_{19}$NO$_5$: C, 66.85; H, 5.61; N, 4.10; found: C, 66.80; H, 5.42; N, 4.15.

(2S,4S)-N-Benzyloxycarbonyl-4-isobutyl-2-(4'-methoxyphenyl)-1,3-oxazolidin-5-one (15) was prepared from sodium N-(para-methoxybenzylidene)-(L)-leucinate (2.71 g, 10.0 mM) and benzyl chloroformate (1.43 mL, 10.0 mM) following general procedure C and obtained as a colourless oil after purification by flash column chromatography, using 25% ethyl acetate/petrol as eluant (3.21 g, 84%, single diastereomer): [α]$_D^{20}$ –30.0 (c 1.0, CHCl$_3$); IR (CHCl$_3$): 1795, 1715 cm$^{-1}$; $^1$H NMR (200 MHz, CDCl$_3$): δ 6.89–7.38 (m, 9H), 6.71 (s, 1H), 5.20 (s, 2H), 4.47 (t, J=7 Hz, 1H), 3.82 (s, 3H), 1.57–1.98 (m, 3H), 0.88–0.92 (m, 6H); $^{13}$C NMR (50.3 MHz, CDCl$_3$): δ 172.5, 160.4, 154.0, 135.3, 129.2, 128.6, 128.3, 127.4, 113.9, 88.8, 68.1, 55.3, 54.4, 42.1, 24.5, 22.3, 22.2; LRMS (NH$_3$): 384 (MH$^+$); HRMS: calcd for C$_{22}$H$_{26}$NO$_5$ (MH$^+$): 384.1811; found: 384.1811.

(2S,4S)-N-Benzoyl-2-(4'-methoxyphenyl)4-methyl-1,3-oxazolidin-5-one (17) was prepared from sodium N-(para-methoxybenzylidene)-(L)-alaninate (2.29 g, 10.0 mM) and benzoyl chloride (1.16 mL, 10.0 mM) following general procedure D and obtained as a white solid after purification by flash column chromatography, using 20% ethyl acetate/petrol as eluant (2.15 g, 69%, mixture of two diastereomers in a ratio of 3:1 by $^1$H NMR). After crystallisation from diethyl ether 17 was obtained as very fine white needles and as a single diastereomer by $^1$H NMR: [α]$_D^{20}$+78.2 (c 1.0, CHCl$_3$); mp 145–147° C.; IR (KBr): 1795, 1735, 1650 cm$^{-1}$; $^1$H NMR (500 MHz, d$_8$-toluene, 90° C.): δ 6.80–7.21 (m, 5H), 6.51–6.53 (m, 4H), 6.43 (s, 1H), 4.44 (q, J=7 Hz, 1H), 3.29 (s, 3H), 1.25 (d, J=7 Hz, 3H); $^{13}$C NMR (50.3 MHz, CDCl$_3$): 6172.5, 170.5, 160.6, 135.2, 130.9, 128.0, 127.6, 126.9, 126.8, 114.0, 90.3, 55.3, 52.7, 18.4; LRMS (NH$_3$): 312 (MH$^+$). Anal. Calcd for C$_{18}$H$_{17}$NO$_4$: C, 69.45; H: 5.46; N, 4.50.; found: C, 69.18; H, 5.55; is N, 4.38.

(2S,4S)-2-(4'-Methoxyphenyl)-4-methyl-N-phenoxyacetyl-1,3-oxazolidin-5-one (18) was prepared from sodium N-(para-methoxybenzylidene)-(L)-alaninate (2.29 g, 10.0 mM) and phenoxyacetyl chloride (1.37 mL, 10.0 mM) following general procedure D and obtained as a colourless oil after purification by flash column chromatography, using 20% ethyl acetate/petroleum ether as eluant (1.87 g, 55%, mixture of two diastereomers in a ratio of 4:1 by $^1$H-NMR). Upon trituration with diethyl ether 18 was obtained as very fine white needles and as a single diastereomer by $^1$H NMR: [α]$_D^{20}$+224 (c 1.0, CHCl$_3$); mp 95–97° C.; IR (KBr): 1795, 1715, 1670 cm$^{-1}$; $^1$H NMR (500 MHz, d$_8$-toluene, 90° C.): δ 6.45–7.09 (m, 9H), 6.44 (s, 1H), 4.50 (q, J=7 Hz, 1H), 4.06 (d, J=14 Hz, 1H), 3.81 (d, J=14 Hz, 1H), 3.31 (s, 3H), 1.41 (d, J=7 Hz, 3H); $^{13}$C NMR (50.3 MHz, CDCl$_3$): δ 172.1, 167.3, 161.4, 156.7, 129.0, 128.5, 128.1, 122.1, 114.6, 114.0, 89.6, 67.8, 55.4, 52.7, 16.1; LRMS (NH$_3$): 342 (MH$^+$). Anal. Calcd for C$_{19}$H$_{19}$NO$_5$: C, 66.86; H, 5.57; N, 4.10; found: C, 66.69; H, 5.59; N, 4.01.

(R/S)-N-Benzoyl-4,4-dimethyl-2-(4'-methoxyphenyl)-1,3-oxazolidin-5-one (19) was prepared from sodium N-(para-methoxybenzylidene)-(2-amino-2'-methyl)-propionate (2.43 g, 10.0 mM) and benzoyl chloride (1.16 mL, 10.0 mM) following general procedure D and obtained as a white solid after purification by flash column chromatography, using 20% ethyl acetate/petrol as eluant (1.71 g, 52%): mp 82–83° C.; IR (KBr). 1800, 1650 cm$^{-1}$; $^1$H NMR (200 MHz, CDCl$_3$): δ 7.10–7.29 (m, 6H), 6.63–6.71 (m, 4H), 3.69 (s, 3H), 1.88 (s, 3H), 1.71 (s, 3H); $^{13}$C NMR (50.3 MHz, CDCl$_3$): 172.5, 169.5, 160.5, 136.4, 130.0, 128.4, 128.2, 128.1, 126.2, 113.9, 89.2, 59.7, 55.2, 25.2, 23.8; LRMS (EI): 326 (MH$^+$). Anal. Calcd for C$_{19}$H$_{19}$NO$_4$: C, 70.15; H, 5.85; N, 4.31; found: C, 69.94; H, 6.08; N, 4.64.

(R/S)-4,4-Dimethyl-2-(4'-methoxyphenyl)-N-phenoxyacetyl-1,3-oxazolidin-5-one (20) was prepared from sodium N-(para-methoxybenzylidene)-(2-amino-2'-methyl)-propionate (2.43 g, 10.0 mM) and phenoxyacetyl chloride (1.37 mL, 10.0 mM) following general procedure D and obtained as a white solid after purification by flash column chromatography, using 20% ethyl acetate/petrol as eluant (2.10 g, 59%): mp 78–82° C.; IR (KBr): 1795, 1680 cm$^{-1}$; $^1$H NMR (200 MHz, CDCl$_3$): 67 7.21–7.40 (m, 5H), 6.77–7.03 (m, 4H), 6.71 (s, 1H), 4.10–4.15 (m, 2H), 3.83 (s, 3H), 1.92 (s, 3H), 1.69 (s, 3H); $^{13}$C NMR (50.3 MHz, CDCl$_3$): 6174.6, 166.4, 161.4, 157.0, 129.7, 128.6, 127.3, 122.0, 114.6, 114.3, 88.5, 68.2, 60.4, 55.4, 24.3, 22.6; LRMS (EI): 356 (MH$^+$). Anal. Calcd for C$_{20}$H$_{21}$NO$_5$: C, 67.60; H, 5.91; N, 3.94; found: C, 67.45; H, 5.91; N, 3.94.

(R/S)-N-Benzoyl-2-(4'-methoxyphenyl)-1,3-oxazolidin-5-one (21) was prepared from sodium N-(para-methoxybenzylidene)-glycinate (2.15 g, 10.0 mM) and benzoyl chloride (1.16 mL, 10.0 mM) following general procedure D and obtained as a white solid after purification by flash column chromatography, using 20% ethyl acetate/petrol as eluant (2.08 g, 70%): mp 130–132° C.; IR (KBr): 1795, 1635 cm$^{-1}$; $^1$H NMR (200 MHz, CDCl$_3$): δ 6.84–7.55 (m, 10H), 4.35 (br, 2H), 3.78 (s, 3H); $^{13}$C NMR (50.3 MHz, CDCl$_3$): 169.4, 169.3, 160.6, 133.6, 131.6, 128.6, 128.3, 127.7, 127.5, 114.3, 89.9, 55.4, 46.7; LRMS (EI): 298 (MH$^+$). Anal. Calcd for $C_{17}H_{15}NO_4$: C, 68.68; H, 5.05; N, 4.71; found: C, 68.62; H, 5.01; N, 4.57.

(2S,4S)-N-Benzyloxycarbonyl4-isopropyl-2-(4'-methoxyphenyl)-1,3-oxazolidin-5-one (22) was prepared from sodium N-(para-methoxybenzylidene)-(L)-valinate (2.57 g, 10.0 mM) and benzyl chloroformate (1.43 mL, 10.0 mM) following general procedure C and obtained as a colourless oil after purification by flash column chromatography, using 25% ethyl acetate/petrol as eluant (2.54 g, 69% mixture of 2 rotamers in a ratio of 2:1, NMR data for major isomer only reported): IR (CHCl$_3$): 1795, 1715 cm$^{-1}$; $^1$H NMR (200 MHz, CDCl$_3$): δ 6.92–7.41 (m, 9H), 6.87 (s, 1H), 5.24 (s, 2H), 4.26 (d, J=5 Hz, 1H), 3.82 (s, 3H), 1.10–1.35 (m, 1H), 0.94 (d, J=5 Hz, 3H), 0.98 (d, J=5 Hz, 3H); $^{13}$C NMR (50.3 MHz, CDCl$_3$): δ 171.2, 160.2, 155.1, 135.3, 129.5, 128.6, 128.0, 127.3, 113.8, 88.4, 68.3, 61.6, 55.3, 31.5, 19.1, 18.4; LRMS (Scan AP$^+$): 370 (MH$^+$); HRMS: calcd for $C_{21}H_{24}NO_5$ (MH$^+$): 370.1654; found: 370.1654.

(4S,5S)4-Benzyl-N-tert-butyloxycarbonyl-5-trifluoromethyl-5-trimethylsilyloxy-1,3-oxazolidine (1a) was prepared from 1 (277 mg, 1.00 mM) following general procedure E and obtained as a white solid after flash column chromatography using 25% chloroform/petrol as eluant (410 mg, 98%, single diastereomer): [α]$_D^{20}$+5.5 (c 1, CHCl$_3$); mp 53–55° C.; IR (KBr): 1705, 1455 cm$^{-1}$; $^1$H NMR (500 MHz, CDCl$_3$): δ 7.19–7.39 (m, 5H), 5.45–5.47 (m, 1H), 4.95 (d, J=5 Hz, 1H), 4.49–4.53 (m, 1H), 3.03 (dd, J=5, 14 Hz, 1H), 2.54–2.70 (m, 1H), 1.15 (s, 9H), 0.25 (s, 9H); $^{13}$C NMR (125.7 MHz, CDCl$_3$): δ 153.0, 137.7, 129.5, 128.2, 126.4, 122.5 (q, $J_{C-F}$=292 Hz), 102.8 (q, $J_{C-F}$=32 Hz), 80.6, 77.5, 61.5, 34.5, 27.6, 1.1; $^{19}$F NMR (235.19 MHz, CDCl$_3$): δ −85.6; LRMS (NH$_3$): 437 (MNH$_4^+$). Anal. Calcd for $C_{19}H_{28}F_3NO_4Si$: C, 54.40; H, 6.73; N, 3.34; found: C, 54.33; H, 6.76; N, 3.56.

(4S,5S)-N-tert-Butyloxycarbonyl4-methyl-5-trifluoromethyl-5-trimethylsilyloxy-1,3-oxazolidine (2a) was prepared from 2 (201 mg, 1.00 mM) following general procedure E and obtained as a colourless oil after flash column chromatography, using 25% chloroform/petrol as eluant (292 mg, 85%, single diastereomer): [α]$_D^{20}$+58.4 (c 0.5, CHCl$_3$); IR (CHCl$_3$): 1700, 1475 cm$^{-1}$; $^1$H NMR (500 MHz, CDCl$_3$): δ 5.17–5.20 (m, 1H), 4.89 (d, J=4 Hz, 1H), 4.26 (q, J=7 Hz, 1H), 1.46 (s, 9H), 1.20 (d, J=7 Hz, 3H), 0.20 (s, 9H); $^{13}$C NMR (125.7 MHz, CDCl$_3$): δ 152.0, 123.5 (q, $J_{C-F}$=289 Hz), 102.2 (q, $J_{C-F}$=32 Hz), 80.6, 77.6, 55.2, 27.0, 14.0, 0.6; $^{19}$F NMR (235.19 MHz, CDCl$_3$): δ −85.6; LRMS (NH$_3$): 361 (MNH$_4^+$); HRMS: calcd for $C_{13}H_{15}F_3NO_4Si$ (MH$^+$): 344.1505; found: 344.1505.

(4S,5S)-N-tert-Butyloxycarbonyl-4-isopropyl-5-trifluoromethyl-5-trimethylsilyloxy-1,3-oxazolidine (3a) was prepared from 3 (229 mg, 1.00 mM) following general procedure E and obtained as a colourless oil after purification by flash column chromatography, using 25% chloroform/petrol as eluant (312 mg, 84%, single diastereomer): [α]$_D^{20}$+24.2 (c 0.5, CHCl$_3$); IR (CHCl$_3$): 1735, 1495 cm$^{-1}$; $^1$H NMR (200 MHz, CDCl$_3$): 85.25–5.47 (m, 1H), 4.69 (br, 1H), 3.80–4.12 (m, 1H), 1.85–2.10 (m, 1H), 1.45 (s, 9H), 1.02 (d, J=7 Hz, 3H), 0.96 (d, J=7 Hz, 3H), 0.20 (s, 9H); $^{13}$C NMR (50.3 MHz, CDCl$_3$): δ 153.9, 122.4 (q, $J_{C-F}$=288 Hz), 102.1 (q, $J_{C-F}$=31 Hz), 81.0, 78.0, 64.9, 27.9, 20.8, 18.6, 18.3, 0.9; $^{19}$F NMR: δ−85.7; LRMS (NH$_3$): 389 (MNH$_{4+}$); HRMS: calculated for $C_{15}H_{29}F_3NO_4Si$ (MH$^+$): 372.1818; found: 372.1818.

(4S,5S)-N-tert-Butyloxycarbonyl-4-isobutyl-5-trifluoromethyl-5-trimethyl-silyloxy-1,3-oxazolidine (4a) was prepared from 4 (243 mg, 1.00 mM) following general procedure E and obtained as a colourless oil after purification by flash column chromatography, using 25% chloroform/petrol as eluant (366 mg, 95%, single diastereomer): [α]$_D^{20}$+22.2 (c 0.5, CHCl$_3$); IR (CHCl$_3$): 1735, 1470 cm$^{-1}$; $^1$H NMR (500 MHz, CDCl$_3$): δ 5.30–5.40 (m, 1H), 4.70–4.81 (m, 1H), 4.25–4.45 (m, 1H), 1.51–1.73 (m, 3H), 1.46 (s, 9H), 0.97 (d, J=6 Hz, 3H), 0.95 (d, J=6 Hz, 3H), 0.19 (s, 9H); $^{13}$C NMR (125.7 MHz, CDCl$_3$): δ 153.0, 122.0 (q, $J_{C-F}$=288 Hz), 102.2 (q, $J_{C-F}$=32 Hz), 81.2, 78.4, 57.9, 37.5, 28.1, 24.4, 22.7, 22.0, 1.0; $^{19}$F NMR: δ −85.6; LRMS (NH$_3$): 403 (MNH$_4$+); HRMS: calcd for $C_{16}H_{31}F_3NO_4Si$ (MH$^+$): 386.1974; found: 386.1974.

(4S,5S)4-(S-Benzylthiomethyl)-N-tert-butyloxycarbonyl-5-trifluoromethyl-5-trimethylsilyloxy-1,3-oxazolidine (5a) was prepared from 5 (323 mg, 1.00 mM) following general procedure E and obtained as a colourless oil after purification by flash column chromatography, using 25% chloroform/petrol as eluant (358 mg, 77%, single diastereomer): [α]$_D^{20}$+25.1 (c 1, CHCl$_3$); IR (CHCl$_3$): 1705, 1495 cm$^{-1}$; $^1$H NMR (500 MHz, CDCl$_3$): δ 7.20–7.35 (m, 5H), 5.23–5.32 (m, 1H), 4.75–4.87 (m, 1H), 4.47–4.55 (m, 1H), 3.77 (s, 2H), 2.63 (dd, J=6, 14 Hz, 1H), 2.49 (dd, J=7, 14 Hz, 1H), 1.50 (s, 9H), 0.17 (s, 9H); $^{13}$C NMR (125.7 MHz, CDCl$_3$): δ 153.4, 138.0, 129.4, 128.9, 127.5, 122.3 (q, $J_{C-F}$=292 Hz), 102.4 (q, $J_{C-F}$=32 Hz), 82.0, 78.9, 59.4, 37.3, 30.5, 28.6, 1.5; $^{19}$F NMR (235.19 MHz, CDCl$_3$): δ −85.6. LRMS (EI): 466 (MH$^+$); HRMS: calcd for $C_{20}H_{31}F_3NO_4SSi$ (MH$^+$): 466.1633; found: 465.1633.

(4S,5S)-4-Benzyl-N-benzyloxycarbonyl-5-trifluoromethyl-5-trimethylsilyloxy-1,3-oxazolidine (6a) was prepared from 65 (311 mg, 1.00 mM) following general procedure E using excess (trifluoromethyl)trimethylsilane (0.38 mL, 2.00 mM, 2.00 eq) and obtained as colourless prisms after purification by flash column chromatography, using 25% chloroform/petrol as eluant (430 mg, 95%, single diastereomer): [α]$_D^{20}$+1.1 (c 1, CHCl$_3$); mp 98–101° C.; IR (KBr): 1715, 1500 cm$^{-1}$; $^1$H-NMR (200 MHz, CDCl$_3$): δ 7.10–7.59 (m, 10H), 5.40–5.45 (m, 1H), 4.95–5.05 (m, 3H), 4.634.67 (m, 1H), 3.05 (dd, J=6, 14 Hz, 1H), 2.69–2.76 (m, 1H), 0.26 (s, 9H); $^{13}$C NMR (125.7 MHz, CDCl$_3$): δ 154.7, 137.7, 136.1, 129.8, 129.2, 128.8, 128.7, 128.6, 127.6, 122.1 (q, $J_{C-F}$=283 Hz), 102.7 (q, $J_{C-F}$=32 Hz), 78.0, 68.0, 61.6, 35.0, 1.6; $^{19}$F NMR (235.19 MHz, CDCl$_3$): δ −85.1; LRMS (NH$_3$): 471 (MNH$_4^+$). Anal. Calcd for $C_{22}H_{26}F_3NO_4Si$: C, 58.26; H, 5.78; N, 3.09. Found: C, 58.59; H, 5.77; N, 3.06.

(4S,5S)-N-Benzyloxycarbonyl4-methyl-5-trifluoromethyl-5-trimethylsililoxy-1,3-oxazolidine (7a) was prepared from 75 (235 mg, 1.00 mM) following general procedure E and obtained as a colourless oil after purification by flash column chromatography, using 25% chloroform/petrol as eluant (260 mg, 69%, single diastereomer): [α]$_D^{20}$+13.1 (c 1, CHCl$_3$); IR (CHCl$_3$): 1715, 1500 cm$^{-1}$; $^1$H NMR (500 MHz, d$_8$-toluene, 90° C.): δ 6.96–7.13 (m, 5H), 5.06 (d, J=4 Hz, 1H), 4.99 (d, J=12 Hz, 1H), 4.95 (d, J=12 Hz, 1H), 4.71 (d, J=4 Hz, 1H), 4.39 (q, J=7 Hz, 1H), 1.15 (d, J=7 Hz, 3H), 0.12 (s, 9H); $^{13}$C NMR (125.7 MHz, CDCl$_3$): 152.9, 135.8, 128.6, 128.3, 127.9, 122.1 (q, $J_{C-F}$=283 Hz), 102.7 (q, $J_{C-F}$=32 Hz), 77.8, 67.5, 55.6, 14.2, 1.0; $^{19}$F NMR (235.19 MHz, CDCl$_3$): −85.4; LRMS (NH$_3$): 395 (MNH$_4{}^+$).

(49S,5S)-N-Benzyloxycarbonyl-4-methoxycarbonylmethyl-5-trifluoromethyl-5-trimethylsilyloxy-1,3-oxazolidine (8a) was prepared from 8 (293 mg, 1.00 mM) following general procedure E and obtained as a colourless oil after purification by flash column chromatography, using 25% chloroform/petrol as eluant (217 mg, 50%, single diastereomer): [α]$_D{}^{20}$+31.7 (c 1.0, CHCl$_3$); IR (CHCl$_3$): 3055, 1720 cm$^{-1}$; $^1$H NMR (500 MHz, d$_8$-toluene, 90° C.): δ 7.14–7.39 (m, 5H), 5.08 (d, J=4 Hz, 1H), 4.91–4.98 (m, 3H), 4.67 (d, J=4 Hz, 1H), 3.35 (s, 3H), 2.51–2.55 (m, 2H), 0.21 (s, 9H); $^{13}$C NMR (125.7 MHz, CDCl$_3$): 169.9, 152.6, 135.7, 128.3, 127.9, 127.2, 122.0 (q, J$_{C-F}$=288 Hz), 102.5 (q, J$_{C-F}$=30 Hz), 78.3, 67.7, 56.8, 51.7, 35.4, 0.85; $^{19}$F NMR (235.19 MHz, CDCl$_3$): −85.3; LRMS (NH$_3$): 436 (MH$^+$). (4S,5S)-N-Benzyloxycarbonyl-4-methoxycarbonylethyl-5-trifluoromethyl-5-trimethylsilyloxy-1,3-oxazolidine (9a) was prepared from 9 (307 mg, 1.00 mM) following general procedure E and obtained as a colourless oil after purification by flash column chromatography, using 25% chloroform/petrol as eluant (330 mg, 73%): [α]$_D{}^{20}$+25.8 (c 0.5, CHCl$_3$); IR (CHCl$_3$): 3055, 1710, 1370 cm$^{-1}$; $^1$H NMR (200 MHz, CHCl$_3$): δ 7.27–7.39 (m, 5H), 5.30–5.40 (m, 1H), 5.15 (s, 2H), 4.85 (s, 1H), 4.36–4.44 (m, 1H), 3.62 (br, 3H), 1.70–2.66 (m, 4H), 0.21 (s, 9H); $^{13}$C NMR (125.7 MHz, CDCl$_3$): δ 173.2, 153.9, 135.7, 128.7, 128.3, 127.9, 122.0 (q, J$_{C-F}$=288 Hz), 102.5 (q, J$_{C-F}$=30 Hz), 77.8, 67.9, 59.0, 51.6, 30.2, 23.8, 1.2; $^{19}$F NMR (235.19 MHz, CDCl$_3$): δ −85.5; LRMS (NH$_3$): 450 (MH$^+$), HRMS: calcd for C$_{19}$H$_{27}$F$_3$NO$_6$Si (MH$^+$): 450.1560; found: 450.1560.

(2S,4S,5S)-N-Benzyloxycarbonyl-4-benzyl-2-tert-butyl-5-trifluoromethyl-5-trimethylsilyloxy-1,3-oxazolidine (10a) was prepared from 10 (367 mg, 1.00 mM) following general procedure E and obtained as a colourless oil after purification by flash column chromatography, using 25% diethyl ether/petrol as eluant (407 mg, 80%, single, diastereomer): [α]$_D{}^{20}$ −5.1 (c 0.5, CHCl$_3$); IR (CHCl$_3$): 1715 cm$^{-1}$; $^1$H NMR (500 MHz, CDCl$_3$): δ 7.19–7.37 (m, 10H), 5.19 (s, 1H), 5.07 (d, J=12 Hz, 1H), 5.06–5.09 (m, 1H), 4.57 (dd, J=6, 7 Hz, 1H), 3.15 (dd, J=7, 14 Hz, 1H), 2.84 (dd, J=6, 14 Hz, 1H), 1.05 (s, 9H), 0.26 (s, 9H); $^{13}$C NMR (125.7 MHz, CDCl$_3$): δ 156.1, 138.3, 135.7, 129.2, 128.4, 128.1, 128.0, 126.2, 122.9 (q, J$_{C-F}$=290 Hz), 101.1 (q, J$_{C-F}$=32 Hz), 97.9, 67.7, 62.7, 36.8, 36.5, 25.9, 1.35; $^{19}$F NMR (235.19 MHz, CDCl$_3$): δ −85.4; LRMS (NH$_3$): 510 (MH$^+$); HRMS: calcd for C$_{26}$H$_{35}$F$_3$NO$_4$Si (MH$^+$): 510.229; found: 510.229.

(2S,4S,5S)-N-Benzyloxycarbonyl-2-tert-butyl-4-methyl-5-trifluoromethyl-5-trimethyl-silyloxy-1,3-oxazolidine (11 a) was prepared from 11 (291 mg, 1.00 mM) following general procedure E and obtained as a colourless oil after purification by flash column chromatography, using 10% diethyl ether/petrol as eluant (164 mg, 38%, single diastereomer): [α]$_D{}^{20}$+24.9 (c 0.75, CHCl$_3$); IR (CHCl$_3$): 1715, 1515 cm$^{-1}$; $^1$H NMR (500 MHz, CDCl$_3$): δ 7.23–7.38 (m, 5H), 5.14 (s, 1H), 5.14–5.16 (m, 2H), 4.41 (q, J=7 Hz, 1H), 1.24 (d, J=7 Hz, 3H), 0.96 (s, 9H), 0.23 (s, 9H); $^{13}$C NMR (50.3 MHz, CDCl$_3$): δ 156.0, 136.1, 128.5, 128.1, 127.8, 122.3 (q, J$_{C-F}$=291 Hz), 100.7 (q, J$_{C-F}$=32 Hz), 97.4, 67.4, 57.1, 36.4, 25.8, 16.0, 1.2; $^{19}$F NMR (235.19 MHz, CDCl$_3$): δ −85.7; LRMS (NH$_3$): 434 (MH$^+$); HRMS: calcd for C$_{20}$H$_3$, F$_3$NO$_4$Si (MH$^+$): 434.1974; found: 434.1974.

(2S,4S,5S)4-Benzyl-N-benzyloxycarbonyl-2-phenyl-5-trifluoromethyl-5-trimethylsilyloxy-1,3-oxazolidine (12a) was prepared from 12$^7$ (387 mg, 1.00 mM) following general procedure E and obtained as a colourless oil after purification by flash column chromatography, using 50% diethyl ether/petrol as eluant (280 mg, 53%, single diastereomer): [α]$_D{}^{20}$ −19.1, (c 0.5, CHCl$_3$); IR (CHCl$_3$): 1720, 1605 cm$^{-1}$; $^1$H NMR (500 MHz, CDCl$_3$): δ 7.10–7.63 (m, 15H), 6.40 (s, 1H), 5.03–5.09 (m, 2H), 4.72–4.74 (m, 1H), 3.14 (dd, J=7, 14 Hz, 1H), 2.75–2.85 (m, 1H); $^{13}$C NMR (125.7 MHz, CDCl$_3$): δ 154.2, 138.5, 137.3, 129.6, 129.3, 129.0, 128.8, 128.3, 128.1, 127.8, 127.7, 126.5, 126.3, 122.6 (q, J$_{C-F}$=290 Hz), 102.1 (q, J$_{C-F}$=33 Hz), 90.3, 67.6, 61.1, 36.4, 1.2; $^{19}$F NMR (235.19 MHz, CDCl$_3$): δ −86.2; LRMS (NH$_3$): 547 (MH$^+$); HRMS: calculated for C$_{28}$H$_{31}$F$_3$NO$_4$Si (MH$^+$): 530.1974; found: 530.1970.

(2S,4S,5S)4-Benzyl-N-benzyloxycarbonyl-2-(4'-methoxyphenyl)-5-trifluoromethyl-5-trimethylsilyloxy-1,3-oxazolidine (13a) was prepared from 13 (417 mg, 1.00 mM) following general procedure F and obtained as a colourless, waxy solid after purification by flash column chromatography, using 25% diethyl ether/petrol as eluant (509 mg, 91%, single diastereomer): [α]$_D{}^{20}$ −155 (c 2.0, CHCl$_3$); mp 41–42° C.; IR (CHCl$_3$): 1710, 1500 cm$^{-1}$; $^1$H NMR (500 MHz, CDCl$_3$): δ 6.97–7.44 (m, 14H), 6.33 (s, 1H), 5.07 (d, J=12 Hz, 1H), 4.91 (d, J=12 Hz, 1H), 4.68–4.72 (m, 1H), 3.88 (s, 3H), 3.16 (dd, J=7, 13 Hz, 1H), 2.80–2.85 (m, 1H), 0.21 (s, 9H); $^{13}$C NMR (125.7 MHz, CDCl$_3$): δ 160.1, 154.1, 137.4, 135.7, 130.7, 129.3, 128.3, 128.0, 127.7, 126.3, 122.1 (q, J$_{C-F}$=290 Hz), 113.7, 102.0 (q, J$_{C-F}$=33 Hz), 90.3, 67.5, 61.1, 55.2, 36.6, 1.2; $^{19}$F NMR (235.19 MHz, CDCl$_3$): δ −85.1; LRMS (EI): 560 (MH$^+$). Anal. Calcd for C$_{29}$H$_{32}$F$_3$NO$_5$Si: C, 62.24; H, 5.76; N, 2.50. Found: C, 61.99; H, 5.68; N, 20 2.46.

(2S,4S)-N-Benzyloxycarbonyl-2-(4'-methoxyphenyl)4-methyl-5-trifluoromethyl-5-trimethylsilyloxy-1,3-oxazolidine (14a) was prepared from 14 (341 mg, 1.00 mM) following general procedure F and obtained as a colourless oil after purification by flash column chromatography, using 25% diethyl ether/petrol as eluant (444 mg, 92%, single diastereomer): IR (CHCl$_3$): 1705, 1615, 1500 cm$^{-1}$; $^1$H NMR (500 MHz, d$_8$-toluene, 90° C.): δ 6.61–7.20 (m, 9H), 6.22 (s, 1H), 4.88 (d, J=12 Hz, 1H), 4.75 (d, J=12 Hz, 1H), 4.47 (q, J=7 Hz, 1H), 3.36 (s, 3H), 1.50 (d, J=7 Hz, 3H), 0.19 (s, 9H); $^{13}$C NMR (125.7 MHz, CDCl$_3$): δ 160.1, 153.5, 135.9, 128.5, 128.2, 127.5, 123.5 (q, J$_{C-F}$=286 Hz), 113.6, 101.6 (q, J$_{C-F}$=32 Hz), 90.2, 67.1, 55.2, 14.6, 1.1; $^{19}$F NMR (235.19 MHz, CDCl$_3$): δ −85.1; LRMS (NH$_3$): 501 (MNH$_4$+); HRMS: calcd for C$_{23}$H$_{29}$F$_3$NO$_5$Si (MH$^+$): 484.1767; found: 484.1767. (2S,4S,5S)-N-Benzyloxycarbonyl-4-isobutyl-2-(4'-methoxyphenyl)-5-trifluoromethyl-5-trimethylsilyloxy-1,3-oxazolidine (15a) was prepared from 15 (383 mg, 1.00 mM) following general procedure F and obtained as a colourless oil after purification by flash column chromatography, using 25% diethyl ether/petrol as eluant (446 mg, 85%, single diastereomer): [α]$_D{}^{20}$ −30.3 (c 1.5, CHCl$_3$); IR (CHCl$_3$): 1710, 1615 cm$^{-1}$; $^1$H NMR (500 MHz, CDCl$_3$): δ 6.91–7.38 (m, 9H), 6.89 (s, 1H), 5.10–5.20 (m, 2H), 4.40–4.42 (m, 1H), 3.83 (s, 3H), 1.34–1.69 (m, 3H), 0.92–1.00 (m, 6H), 0.21 (s, 9H); $^{13}$C NMR (125.7 MHz, CDCl$_3$): δ 160.1, 154.1, 135.6, 130.6, 128.4, 128.1, 127.9, 122.9 (q, J$_{C-F}$=286 Hz), 113.6, 102.1 (q, J$_{C-F}$=33 Hz), 90.1, 67.5, 57.6, 55.2, 39.8, 24.4, 22.4, 22.2, 1.1; $^{19}$F NMR (235.19 MHz, CDCl$_3$): δ −87.6; LRMS (NH$_3$): 543 (MNH$_4{}^+$); HRMS: calcd for C$_{26}$H$_{35}$F$_3$NO$_5$Si (MH$^+$): 526.2236; found: 526.2236.

(2S,4S,5S)-N-Benzoyl-4-benzyl-2-tert-butyl-5-trifluoromethyl-5-trimethylsilyloxy-1,3-oxazolidine (16a) was prepared from 16$^8$ (337 mg, 1.00 mM) following general procedure E and obtained as a colourless oil after purification by flash column chromatography, using 25% diethyl ether/petrol as eluant (340 mg, 71%): $[\alpha]_D^{20}$ −33.0 (c 1.0, CHCl$_3$); IR (CHCl$_3$): 1665, 1600 cm$^{-1}$; $^1$H NMR (500 MHz, CDCl$_3$): δ 7.09–7.51 (m, 8H), 6.70–6.81 (m, 2H), 5.69 (s, 1H), 4.24 (dd, J=2, 6 Hz, 1H), 3.35 (dd, J=6, 7 Hz, 1H), 2.93 (dd, J=2, 7 Hz, 1H), 1.12 (s, 9H), 0.21 (s, 9H); $^{13}$C NMR (50.3 MHz, CDCl$_3$): δ 174.8, 137.0, 130.4, 129.1, 128.7, 128.4, 126.8, 126.6, 126.5, 121.5 (q, $J_{C-F}$=292 Hz), 100.7 (q, $J_{C-F}$=32 Hz), 96.6, 63.3, 37.9, 26.0, 14.0, 1.2; $^{19}$F NMR (235.19 MHz, CDCl$_3$): δ − 85.7; LRMS (NH$_3$): 480 (MH$^+$). Anal. calcd for C$_{25}$H$_{32}$F$_3$NO$_3$Si: C: 62.61, H: 6.72, N: 2.92%; found: C: 62.52, H: 6.44, N: 2.92%.

(2S,4S,5S)- and (2S,4S,5R)-N-Benzoyl-2-(4'-methoxyphenyl)-4-methyl-5-trifluoromethyl-5-trimethylsilyloxy-1,3-oxazolidine (17a) were prepared from 17 (311 mg, 1.00 mM) following general procedure F and obtained as a colourless oil after purification by flash column chromatography, using 25% diethyl ether/petrol as eluant (425 mg, 94%, mixture of two diastereomers in a ratio of 1.5:1 by $^1$H and $^{19}$F NMR analysis): IR (CHCl$_3$): 1650, 1495 cm$^{-1}$; $^1$H NMR (500 MHz, d$_8$-toluene, 90° C.): 6.41–7.23 (m, 10H), 4.81 (q, J=6 Hz, 1H, minor diastereomer), 4.66 (q, J=7 Hz, 1H, major diastereomer), 3.36 (s, 3H, major diastereomer), 3.28 (s, 3H, minor diastereomer), 1.34 (d, J=6 Hz, 3H, minor diastereomer), 1.27 (d, J=7 Hz, 3H, major diastereomer), 0.24 (s, 9H, minor diastereomer), 0.07 (s, 9H, major diastereomer); $^{13}$C NMR (125.7 MHz, CDCl$_3$, all signals were very broad): δ 170.5, 159.9, 135.6, 130.1, 128.7, 128.5, 127.9, 127.1, 126.3, 122.8 (q, $J_{C-F}$=290 Hz), 102.2 (q, $J_{C-F}$=33 Hz), 90.2, 55.3, 16.2, 1.1; $^{19}$F NMR (235.19 MHz, CDCl$_3$): 67 −85.0/−86.0; LRMS (EI): 454 (MH$^+$); HRMS calcd for C$_{22}$H$_{27}$F$_3$NO$_4$Si: 454.1661; found: 454.1661.

(2S,4S,5S)- and (2S,4S,5R)-2-(4'-Methoxyphenyl)-4-methyl-N-phenoxyacetyl-5-trifluoro-methyl-5-trimethylsilyloxy-1,3-oxazolidine (18a) were prepared from 18 (341 mg, 1.00 mM) following general procedure F and obtained as a colourless oil after purification by flash column chromatography, using 25% diethyl ether/petrol as eluant (410 mg, 85%, mixture of two diastereomers in a ratio of 1.3:1 by $^1$H and $^{19}$F NMR analysis): IR (CHCl$_3$): 1655, 1615 cm$^{-1}$; $^1$H NMR (250 MHz, d$_8$-toluene, 90° C.): δ 6.56–7.21 (m, 18H), 6.69 (s, 1H, minor diastereomer), 6.67 (s, 1H, major diastereomer), 4.97 (d, J=12 Hz, 1H, minor diastereomer), 4.91 (d, J=12 Hz, 1H, major diastereomer), 4.88 (d, J=12 Hz, 1 H, minor diastereomer), 4.74 (d, J=12 Hz, 1 H, major diastereomer), 4.62 (q, J=7 Hz, 1 H, major diastereomer), 4.47 (q, J=7 Hz, 1 H, minor diastereomer), 3.31 (s, 3H, major diastereomer), 3.30 (s, 3H, minor diastereomer), 1.50 (d, J=7 Hz, 3H, major diastereomer), 1.34 (d, J=7 Hz, 3H, minor diastereomer), 0.13 (s, 9H, major diastereomer), 0.05 (s, 9H, 5 major diastereomer); $^{13}$C NMR (125.7 MHz, CDCl$_3$): δ 160.4, 160.1, 153.5, 152.4, 135.9, 130.3, 128.5, 128.4, 128.2, 127.9, 127.5, 124.0 (q, $J_{C-F}$=290 Hz), 123.5 (q, $J_{C-F}$=287 Hz), 113.7, 113.6, 101.7 (q, $J_{C-F}$=32 Hz), 101.6 (q, $J_{C-F}$=32 Hz), 90.3, 90.2, 67.2, 67.1, 55.2, 55.1, 16.2, 14.6, 1.07; $^{19}$F NMR (235.19 MHz, d$_8$-toluene, 90° C.): δ −89.0 (major diastereomer), −90.2 (minor diastereomer); LRMS (NH$_3$): 501 (MNH$_4^+$); HRMS: calcd for C$_{23}$H$_{27}$F$_3$NO$_5$Si (MH$^+$): 484.1767, found: 484.1767.

(2RS,5RS)-N-Benzoyl-4,4-dimethyl-2-(4'-methoxyphenyl)-5-trifluoromethyl-5-trimethylsilyloxy-1,3-oxazolidine (19a) was prepared from 19 (325 mg, 1.00 mM) following general procedure F and obtained as a colourless oil after purification by flash column chromatography, using 15% ethyl acetate/petrol as eluant (336 mg, 72%, single pair of enantiomers): mp 120–123° C.; IR (KBr): 1650, 1495 cm$^{-1}$; $^1$H NMR (500 MHz, CDCl$_3$): δ 6.65–7.85 (m, 9H), 6.19 (s, 1H), 3.79 (s, 3H), 1.62 (s, 6H), 0.18 (s, 9H); $^{13}$C NMR (125.7 MHz, CDCl$_3$): δ 169.6, 160.0, 137.5, 132.0, 129.7, 128.1, 126.4, 122.1 (q, $J_{C-F}$=293 Hz), 113.5, 103.8 (q, $J_{C-F}$=31 Hz), 90.5, 65.1, 55.2, 23.1, 20.3, 1.2; $^{19}$F NMR (235.19 MHz, CDCl$_3$): δ −77.7; LRMS (NH$_3$): 468 (MH$^+$); HRMS: calcd for C$_{23}$H$_{29}$F$_3$NO$_4$Si (MH$^+$): 468.1818; found: 468.1818.

(2R-S,5RS)-4,4-Dimethyl-2-(4'-methoxyphenyl)-N-phenoxyacetyl-5-trifluoromethyl-5-trimethylsilyloxy-1,3-oxazolidine (20a) was prepared from 20 (355 mg, 1.00 mM) following general procedure F and obtained as a white solid after purification by flash column chromatography, using 25% ethyl acetate/petrol as eluant (372 mg, 75%, single pair of enantiomers): mp 89–92° C.; IR (KBr): 1650, 1515, 1495 cm$^{-1}$; $^1$H NMR (500 MHz, CDCl$_3$): δ 6.39–7.48 (m, 9H), 6.29 (s, 1H), 3.90.4.14 (m, 2H), 3.84 (s, 3H), 1.67 (s, 3H), 1.66 (s, 3H), 0.15 (s, 9H); $^{13}$C NMR (125.7 MHz, CDCl$_3$): δ 166.7, 160.8, 157.3, 129.5, 129.1, 128.9, 122.8 (q, $J_{C-F}$= 290 Hz), 121.6, 114.3, 114.2, 103.4 (q, $J_{C-F}$=30 Hz), 89.1, 68.4, 66.1, 55.3, 22.9, 19.9, 1.2; $^{19}$F NMR (235.19 MHz, CDCl$_3$): δ −77.7; LRMS (NH$_3$): 498 (MH$^+$). Anal. Calcd for C$_{24}$H$_3$F$_3$NO$_5$Si: C, 57.93; H, 6.08; N, 2.82. Found: C, 58.07; H, 5.91; N, 2.91.

(2RS, 5RS)-N-benzoyl-2-(4'-methoxyphenyl)-5-trifluoromethyl-5-trimethylsilyloxy-1,3-oxazolidine (21a) was prepared from 21 (150 mg, 0.46 mM) following general procedure F and obtained as a white solid after purification by preparative thin layer chromatography, using 25% ethyl acetate/petrol as eluant (151 mg, 75%, 21 was unstable and only characterised by its $^1$H and $^{19}$F NMR spectrum):$^1$H NMR (500 MHz, CDCl$_3$): δ 6.81–7.50 (m, 9H), 6.70 (s, br, 1H), 3.71–3.91 (m, 5H), 0.10–0.26 (s, 9H); $^{19}$F NMR (235.19 MHz, CDCl$_3$): δ −85.2. (2S,4S,5S)-N-Benzyloxycarbonyl-4-isopropyl-2-(4'-methoxyphenyl)-5-trifluoromethyl-5-trimethylsilyloxy-1,3-oxazolidine (22a) was prepared from 22 (369 mg, 1.00 mM) following general procedure F and obtained as a colourless oil after purification by flash column chromatography, using 25% diethyl ether/petrol as eluant (414 mg, 81%, single diastereomer): IR (CHCl$_3$): 1720, 1615 cm$^{-1}$; $^1$H NMR (500 MHz, CDCl$_3$): δ 6.87–7.34 (m, 9H), 6.24 (s, 1H), 5.15–5.20 (m, 2H), 4.04 (d, br, J=8.5 Hz, 1H), 3.83 (s, 3H), 1.91–1.98 (m, 1H), 1.05 (d, J=6 Hz, 3H), 087–0.97 (m, 3H) 0.21 (s, 9H); $^{13}$C NMR (125.7 MHz, CDCl$_3$): δ 159.9, 155.1, 136.0, 130.7, 128.5, 128.1, 128.0, 127.7, 122.9 (q, $J_{C-F}$=290 Hz), 113.5, 102.3 (q, $J_{C-F}$=32 Hz), 90.0, 67.6, 64.2, 55.2, 28.8, 20.6, 19.5, 1.2; $^{19}$F NMR (235.19 MHz, CDCl$_3$): δ −85.6; LRMS (Scan AP$^+$): 512 (MNH$_4^+$); HRMS: calcd for C$_{25}$H$_{33}$F$_3$NO$_5$Si (MH$^+$): 512.2080; found: 512.2080.

(3S,)-3-Amino-N-benzyloxycarbonyl4-phenyl-1,1,1-trifluorobutan-2-one (13c) was prepared following general procedure H and obtained as fine white needles after crystallisation from diethyl ether/petrol (374 mg, 98%, mixture of ketone and hydrate in a ratio of 2:3 by $^{19}$F NMR in CDCl$_3$. The assignment of NMR signals to ketone or hydrate is based on this ratio and the integrals in the $^1$H NMR spectrum: $[\alpha]_D^{20}$=+23.1 (c 0.5, CHCl$_3$). mp 86–89° C. IR: 3400–2800, 1770, 1705, 1680 cm$^{-1}$; $^1$H NMR (500 MHz, CDCl$_3$): δ 6.76–7.34 (m, 2×10H), 5.29–5.31 (m, 5H), 4.42/4.48 (2×ABq, $J_{A-B}$=13 Hz, 2×2H), 3.82–3.86 (m, 1H), 3.26–3.30 (m, 1H), 2.97–3.02 (m, 2×1H); $^{13}$C NMR (125.7 MHz, CDCl$_3$): δ 190.1 (q, $J_{C-F}$=35 Hz), 156.9, 156.8, 137.0, 133.7, 129.8, 129.2, 129.0, 128.9, 128.8, 127.8, 127.1, 122.6 (q, $J_{C-F}$=289 Hz), 122.5, 122.3, 115.0 (q, $J_{C-F}$=293 Hz), 114.8, 114.6, 94.5 (q, $J_{C-F}$=31 Hz), 67.1, 67.0, 57.8, 54.3, 36.2, 33.4; $^{19}$F NMR (235.19 MHz, CDCl$_3$): δ −76.2, −82.6; LRMS (EI): 352 (MH$^+$). Anal. Calcd for C$_{18}$H$_{16}$F$_3$NO$_3$: C, 61.54; H, 4.56; N, 3.99. Found: C, 61.30; H, 4.86; N, 3.66.

(3S)-3-Amino-N-benzyloxycarbonyl4-methyl-1,1,1-trifluorobutan-2-one (14c) was prepared following general procedure H and obtained as a slowly solidifying oil after purification by preparative thin layer chromatography using 25% ethyl acetate/petrol as eluant (190 mg, 69%, mixture of ketone and hydrate in a ratio of 3:1 by $^{19}$F NMR in CDCl$_3$). The assignment of NMR signals to ketone or hydrate is based on this ratio and the integrals in the $^1$H NMR spectrum): IR: 3500–3000, 1770, 1685, 1535 cm$^{-1}$; $^1$H NMR (500 MHz, CDCl$_3$): δ 7.32–7.40 (m, 2×5H), 5.31 (d, J=25 7 Hz, 1H, ketone), 5.11–5.15 (m, 5H), 4.86 (qui, J=7 Hz, 1H, ketone), 3.99 (qui, J=7 Hz, 1H, hydrate), 1.48 (d, J=7 Hz, 1H, ketone), 1.37 (d, J=7 Hz, 1H, hydrate); $^{13}$C NMR (125.7 MHz, CDCl$_3$): δ 190.1 (q, J$_{C-F}$=35 Hz), 158.5, 155.3, 135.7, 135.4, 128.6, 128.5, 128.4, 128.2, 127.8, 127.1, 123.1 (q, J$_{C-F}$=288 Hz), 115 .5 (q, J$_{C-F}$=293 Hz), 95.2–95.5 (m), 67.9, 67.5, 51.8, 51.6, 18.9, 16.8; $^{19}$F NMR (235.19 MHz, CDCl$_3$): δ −76.4, −82.6; LRMS (Scan AP$^+$): 298 (MNa$^+$); HRMS: calcd for C$_{12}$H$_{13}$F$_3$NO$_3$ (MH$^+$): 276.085; found: 276.085.

(3S)-3-Amino-N-benzyloxycarbonyl-4-methyl-1,1,1-5 trifluorohexan-2-one (15c) was prepared following general procedure H and obtained as a slowly solidifying oil after purification by preparative thin layer chromatography using 25% ethyl acetate/petrol as eluant (174 mg, 55%, mixture of ketone and hydrate in a ratio of 9:1 by $^{19}$F NMR in CDCl$_3$. Only the signals for the ketone form were observed in the $^1$H and $^{13}$C NMR io spectra: IR: 3500–3000, 1770, 1680 cm$^{-1}$; $^1$H NMR (500 MHz, CDCl$_3$): δ 7.33–7.39 (m, 5H), 5.11–5.15 (m, 2H), 4.71–4.87 (m, 1H), 1.60–1.81 (m, 3H), 1.10 (d, J=7 Hz, 1H), 0.97 (d, J=7 Hz, 1H); $^{13}$C NMR (125.7 MHz, CDCl$_3$): δ 191.1 (q, J$_{C-F}$=33 Hz), 155.8, 135.8, 128.6, 128.4, 128.2, 115.1 (q, J$_{C-F}$=293 Hz), 67.5, 54.6, 39.6, 24.9, 23.1, 21.1; $^{19}$F NMR (235.19 MHz, CDCl$_3$): δ −76.2, −81.9; LRMS (NH$_3$): 318 (MH$^+$); HRMS: calcd for C$_{15}$H$_{18}$F$_3$NO$_3$ (MH$^+$): 318.1317; found: 318.1317.

(3S)-3-Amino-N-benzoyl-4-phenyl-1,1,1-trifluorobutan-2-one (16c) was prepared following general procedure H and obtained as fine white needles after from ethyl acetate/hexane (244 mg, 76%, mixture of hydrate and ketone in a ratio of 20:1 by $^{19}$F NMR in d$_6$-acetone. Only the signals for the hydrate form were observed in the $^1$H and $^{13}$C NMR spectra): [α]$_D^{20}$=−154.0 (c 0.5, acetone). mp 158–160° C. IR: 3400–2800, 1770, 1705, 1680 cm$^{-1}$. NMR spectroscopic data for hydrate form: $^1$H NMR (500 MHz, d$_6$-acetone): δ 8.06 (d, J=8 Hz, 1H), 7.16–7.51 (m, 10H), 6.80 (s, 1H), 4.34 (ddd, J=3, 8, 12 Hz, 1H), 3.38 (dd, J=3, 14 Hz, 1H), 3.27 (dd, J=12, 14 Hz, 1H); $^{13}$C NMR (125.7 MHz, d$_6$-acetone): δ 170.8, 139.6, 134.6, 130.6, 130.1, 129.1, 128.2, 127.2, 124.9 (q, J$_{C-F}$=289 Hz), 95.4 (q, J$_{C-F}$=293 Hz), 58.9, 33.5; $^{19}$F NMR (235.19 MHz, CDCl$_3$): δ −82.7; LRMS (EI): 322 (MH$^+$); HRMS: calcd for C$_{17}$H$_{15}$F$_3$NO$_2$ (MH$^+$): 322.1055; found: 322.1015.

(3S)-3-Amino-N-benzoyl-1,1,1-trifluorobutan-2-one (1 7c) was prepared following general procedure H and obtained as colourless 5 crystals after crystallisation from diethyl ether/petroleum (208 mg, 85%, mixture of ketone and hydrate in a ratio of 2:3 by $^{19}$F NMR in d$_6$-acetone. The assignment of NMR signals to ketone or hydrate is based on this ratio and the integrals in the $^1$H NMR spectrum): mp 115° C. IR: 3400–3000, 1625 cm$^{-1}$. $^1$H NMR (500 MHz, d$_6$-acetone): δ 7.69–7.80 (m, 4H), 7.37–7.54 (m, 6H), 6.95 (d, br, J=7 Hz, ketone), 6.85 (d, br, J=7 Hz, hydrate), 5.18 (qui, J=7 Hz, 1H, ketone), 4.22 (qui, J=7 Hz, 1H, hydrate), 1.56 (d, J=7 Hz, 3H, ketone), 1.47 (d, J=7 Hz, 3H, hydrate); $^{13}$C NMR (125.7 MHz, d$_6$-acetone): δ 192.0–192.3 (m), 170.4, 167.1, 132.3, 132.1, 128.6, 127.6, 127.3, 127.1, 123.3, 122.6 (q, J$_{C-F}$=291 Hz), 122.4, 116.8 (q, J$_{C-F}$=292 Hz), 94.8 (q, J$_{C-F}$=32 Hz), 51.5, 50.4, 16.4, 14.8; $^{19}$F NMR (235.19 MHz, d$_6$-acetone): δ −76.4/−82.2; LRMS (EI): 246 (MH$^+$); HRMS: calcd for C$_{11}$H$_{10}$F$_3$NO$_2$ (MH$^+$): 246.0742; found: 246.0749.

(3S)-3-Amino-N-phenoxyacetyl-1,1,1-trifluorobutan-2-one (18c) was prepared following general procedure H and obtained as 20 colourless crystals after crystallisation from diethyl ether/petrol (208 mg, 85%, mixture of ketone and hydrate in a ratio of 3:2 by $^{19}$F NMR in CDCl$_3$. The assignment of NMR signals to ketone or hydrate is based on this ratio and the integrals in the $^1$H NMR spectrum): [α]$_D^{20}$=+16.6 (c 0.5, CHCl$_3$); mp 75–77° C.; IR (CHCl$_3$): 1770, 1600 cm$^{-1}$; $^1$H NMR (500 MHz, CDCl$_3$): δ 6.93–7.37 (m, 6H), 5.12 (qui, 1H, ketone), 4.55 (s, 2H, ketone), 4.54 (s, 2H, hydrate), 4.22 (qui, J=5 Hz, 1H, hydrate), 1.44 (d, J=5 Hz, 3H, ketone), 1.40 (d, J=5 Hz, 3H, hydrate); $^{13}$C NMR (125.7 MHz, CDCl$_3$): δ 190.2 (q, J$_{C-F}$=35 Hz), 171.6, 168.2, 157.0, 156.8, 129.8, 122.5 (q, J$_{C-F}$=292 Hz), 122.6, 122.4, 114.7, 115.6 (q, J$_{C-F}$=289 Hz), 94.6 (q, J$_{C-F}$=30 Hz), 51.2, 49.8, 16.6, 14.6; α$_F$ (235.19 MHz, CDCl$_3$): −76.5, −82.4; m/z (NH$_3$): 276 (MH$^+$); Anal calcd for C$_{12}$H$_{12}$F$_3$NO$_3$: C: 52.37, H: 4.39, N: 5.09%; found: C: 52.51, H: 4.25, N: 5.09%.

3-Amino-N-benzoyl-3-methyl-1,1,1-trifluorobutan-2-one (19c) was prepared following general procedure H and obtained as colourless prisms after crystallisation from diethyl ether/petrol (176 mg, 68%, mixture of ketone and hydrate in a ratio of 7:1 by $^{19}$F NMR in CDCl$_3$. Only the signals for the ketone form were observed in the $^1$H and $^{13}$C NMR spectra): mp 178–180° C. IR: 3300–3100, 1730, 1630 cm$^{-1}$. NMR data for ketone: $^1$H NMR (500 MHz, CDCl$_3$): δ 7.45–7.78 (m, 5H), 6.49 (s, 1H), 1.66 (s, 6H); $^{13}$C NMR (125.7 MHz, CDCl$_3$): δ 189.9 (q, J$_{C-F}$=32 Hz), 167.6, 136.3, 128.5, 126.1, 116.2 (q, J$_{C-F}$=294 Hz), 113.9, 24.1, 23.7; $^{19}$F NMR (235.19 MHz, CDCl$_3$): δ −73.0; LRMS (EI): 260 (MH$^+$). Anal calcd for C$_{12}$H$_{12}$F$_3$NO$_2$: C: 55.60, H: 4.68, N: 5.40%; found: C: 55.46, H: 4.72, N: 5.41%.

3-Amino-3-methyl-N-phenoxyacetyl-1,1,1-trifluorobutan-2-one (20c) was prepared following general procedure H and obtained as colourless prisms after crystallisation from diethyl ether/petrol (254 mg, 88%, mixture of ketone and hydrate in a ratio of 5:1 by $^{19}$F NMR in CDCl$_3$. The assignment of NMR signals to ketone or hydrate is based on this ratio and the integrals in the $^1$H NMR spectrum): IR: 3200–3000, 1750, 1650 cm$^{-1}$; $^1$H NMR (500 MHz, CDCl$_3$): δ 6.92–7.36 (m, 12H), 4.51 (s, 2H, ketone), 4.50 (s, 2H, hydrate), 1.60 (s, 6H, ketone), 1.55 (s, 6H, hydrate); $^{13}$C NMR: δ 189.9 (q, J$_{C-F}$=33 Hz), 171.4, 168.4, 156.9, 156.7, 129.9, 129.6, 122.7, 122.5, 116.1 (q, J$_{C-F}$=293 Hz), 114.8, 114.7, 95.5–95.7(m), 67.0, 66.9, 60.1, 58.5, 24.0, 23.6; $^{19}$F NMR (235.19 MHz, CDCl$_3$): δ 72.9, 79.7; LRMS (EI): 290 (MH$^+$); HRMS: calcd for C$_{13}$H$_{13}$F$_3$NO$_3$ (MH$^+$): 290.1004; found: 290.1004.

3-Amino-N-benzoyl-1,1,1-trifluoropropan-2-one hydrate (21c) was prepared following general procedure H and obtained as a white solid after crystallisation from diethyl ether/petroleum (176 mg, 68%): IR: 3500–3000, 1625 cm$^{-1}$; $^1$H NMR (500 MHz, d$_6$-acetone): δ 8.44 (br, 1H), 7.48–7.98 (m, 5H), 3.79 (d, J=6 Hz, 2H); $^{13}$C NMR (125.7 MHz, CDCl$_3$): δ 171.5, 134.0, 132.9, 129.4, 128.4, 124.6 (q, J$_{C-F}$=294 Hz), 94.4 (q, J$_{C-F}$=288 Hz), 46.0; $^{19}$F NMR (235.19 MHz, CDCl$_3$): δ −85.7; LRMS (EI): 232 (MH$^+$); HRMS: calcd for C$_{10}$H$_9$F$_3$NO$_2$ (MH$^+$): 232.0585; found: 232.0585.

(3S)-3-Amino-N-benzyloxycarbonyl4-methyl-1,1,1-trifluoropentan-2-one (22c) was prepared from 22b (11 mg, 0.025 mM) following general procedure H and obtained as a colourless oil after purification by preparative thin layer chromatography (4.9 mg, 65%): IR: 1785, 1705, 1680 cm$^{-1}$; $^1$H NMR (500 MHz, CDCl$_3$): δ 7.26–7.34 (m, 5H), 5.25–5.26 (m, 1H), 5.13–5.15 (m, 2H), 4.84 (dd, J=4, 9 Hz, 1H), 2.32–2.36 (m, 1H), 1.09 (d, J=7 Hz, 3H), 0.85 (d, J=7 Hz, 3H); $^{13}$C NMR (125.7 MHz, CDCl$_3$): δ 189.2 (q, $J_{C-F}$=31 Hz), 156.1, 135.8, 128.6, 128.4, 128.2, 115.4 (q, $J_{C-F}$=281 Hz), 67.5, 60.9, 29.3, 19.2, 16.2; $^{19}$F NMR (235.19 MHz, CDCl$_3$): δ 76.8; LRMS (Scan AP$^+$): 302 (M—H); HRMS: calcd for C$_{14}$H$_{17}$F$_3$NO$_3$ (MH$^+$): 304.1170; found: 304.1170.

(3S)-3-Amino-4-phenyl-1,1,1-trifluorobutan-2-one hydrochloride salt (13d): To a solution of 13c (130 mg, 0.37 mM) in ethanol (5 mL) was added Pd-C catalyst (30 mg) and 1 eq of 1.0 N hydrochloric acid (0.37 mL of a 1.0 N convol® standard solution). The mixture was placed under a hydrogen balloon and stirred for three hours after which time all starting material had been consumed by tlc. After diluting with ethanol (15 mL) the catalyst was filtered off through a plug of Celite®. The solvents were removed in vacuo and the residue taken up in aqueous hydrochloric acid. After extraction with diethyl ether the aqueous layer was reduced in vacuo and 13d was obtained as a pale yellow solid (90 mg, quantitative yield): [α]$_D^{20}$=–37.0 (c=1.0, 1.0 M HCl); $^1$H NMR (500 MHz, D$_2$O): δ 7.34–7.44 (m, 5H), 3.83 (dd, J=3, 11 Hz, 1H), 3.39 (dd, J 3, 14 Hz, 1H), 2.86 (dd, J=11, 14 Hz, 1H); $^{13}$C NMR (125.7 MHz, D$_2$O): δ 135.2, 130.0, 129.9, 128.4, 123.2 (q, $J_{C-F}$=291 Hz), 92.4 (q, $J_{C-F}$=32 Hz), 57.4, 33.3; $^{19}$F NMR (235.19 MHz, D$_2$O): –81.7. LRMS (EI): 218 (free amine).

(±)-3-Amino-4-methyl-1,1,1-trifluorobutan-2-one hydrochloride salt (14d): To a solution of 14c (108 mg, 0.39 mM) in ethanol (5 mL) was added Pd-C catalyst (30 mg) and 1 eq of 1.0 N hydrochloric acid (0.39 mL of a 1.0 N convol® standard solution). The mixture was placed under a hydrogen balloon and stirred for two hours after which time all starting material had been consumed by tlc. After diluting with 15 mL of ethanol the catalyst was filtered off through a plug of Celite®. The solvents were removed in vacuo and the residue taken up in aqueous hydrochloric acid. After extraction with diethyl ether the aqueous layer was reduced in vacuo and 14d was obtained as a pale yellow solid (70 mg, quantitative yield): $^1$H NMR (500 MHz, D$_2$O): δ 3.66 (q, J=7 Hz, 1H), 1.35 (d, J=7 Hz, 3H); $^{13}$C NMR (125.7 MHz, D$_2$O): δ 122.9 (q, $J_{C-F}$=288 Hz), 92.2 (q, $J_{C-F}$=32 Hz), 51.1, 12.6; $^{19}$F NMR (235.19 MHz, D$_2$O): –82.2.

(3S)-3-Amino-4-methyl-1,1,1-trifluoropentan-2-one hydrochloride salt (22d): To a solution of 22c (303 mg, 1.00 mM) in ethanol (10 mL) was added Pd-C catalyst (110 mg) and 1 eq of 1.0 N hydrochloric acid (1.00 mL of a 1.0 N convol® standard solution). The mixture was placed under a hydrogen balloon and stirred for three hours after which time all starting material had been consumed by tlc. After diluting with ethanol (15 mL) the catalyst was filtered off through a plug of Celite®. The solvents were removed in vacuo and the residue taken up in aqueous hydrochloric acid. After extraction with diethyl ether the aqueous layer was reduced in vacuo and 22d was obtained as a pale yellow solid (110 mg, 53%): $^1$H NMR (500 MHz, D$_2$O): δ 3.41 (d, J=3.5 Hz, 1H), 2.34–2.40 (m, 1H), 1.09 (d, J=7 Hz, 3H), 1.04 (d, J=7 Hz, 3H); $^{13}$C NMR (125.7 MHz, D$_2$O): δ 122.8 (q, $J_{C-F}$=288 Hz), 92.3 (q, $J_{C-F}$=32 Hz), 59.2, 25.6, 20.3, 15.8; $^{19}$F NMR (235.19 MHz, D$_2$O): –82.7.

Benzyloxycarbonyl-(L)-phenylalanyl-N-[(3RS)-(4-phenyl-1,1,1-trifluorobutan-2-one)] amide (23): To a cooled solution (–15° C.) of N-benzyloxycarbonyl-(L)-phenylalanine (87 mg, 0.29 mM) and triethylamine (41 μL, 0.29 mM) in THF was added ethyl chloroformate (27 μL, 0.28 mM) followed by the formation of a white precipitate. After 10 minutes a pre-cooled solution (–15° C.) of (3RS)-3-amino-4-phenyl-1,1,1-trifluorobutan-2-one hydrochloride salt (65 mg, 0.26 mM) and triethylamine (35 μl, 0.26 mM) was added and stirring continued at –10° C. for 30 minutes and then for another 30 minutes allowing to warm slowly to room temperature. After addition of ethyl acetate (15 mL) the organic layer was washed with aqueous hydrochloric acid (10 mL), saturated sodium bicarbonate solution (15 mL) and dried over magnesium sulphate. The solvents were evaporated in vacuo and the product obtained as a white solid after purification by preparative thin layer chromatography using 50% petrol/diethyl ether as eluant (39 mg, 30%, two diastereomers in a ratio of 1:1 and as a 1:4 mixture of ketone and hydrate by $^{19}$F NMR in CDCl$_3$): $^1$H NMR (500 MHz, d$_6$-acetone): δ 7.75 (d, br, J=8.5 Hz, 1H), 7.66 (d, br, J=8.5 Hz, 1H), 7.09–7.39 (4×15H), 6.41 (d, br, J=8 Hz, 1H), 6.36 (d, br, J=8 Hz, 1H), 4.94–5.06 (m, 4×3H), 4.25–4.52 (m, 4×2H), 2.60–3.01 (m, 4×4H); $^{13}$C NMR (125.7 MHz, CDCl$_3$, only the signals for the hydrated form were observed): δ 174.6, 174.4, 156.8, 139.3, 138.6, 138.4, 138.3, 138.1, 137.8, 130.3, 130.2, 130.1, 130.0, 129.4, 129.2, 129.1, 129.0, 128.6, 128.5, 128.4, 127.3, 127.2, 127.1, 124.8, 94.1–95.7, 66.7, 66.6, 57.3, 57.2, 57.1, 38.5, 38.4, 34.7, 34.3; $^{19}$F NMR (235.19 MHz, d$_6$-acetone): δ –82.3, –82.5; m/z (NH$_3$): 499 (MH$^+$); HRMS calculated for C$_{27}$H$_{25}$F$_3$N$_2$O$_4$: 499.1844; found: 499.1845.

N-Benzyloxycarbonyl-(L)-alanyl-N-[(3RS)-3-(4-phenyl-1,1,1-trifluorobutan-2-one)] amide (24): To a cooled solution (–15° C.) of N-benzyloxycarbonyl-(L)-alanine (49 mg, 0.22 mM) and triethylamine (31 μL, 0.22 mM) in dry THF was added ethyl chloroformate (21 μL, 0.22 mM) followed by the formation of a white precipitate. After 10 minutes a pre-cooled solution (–15° C.) of (3RS)-3-amino-4-phenyl-1,1,1-trifluorobutan-2-one hydrochloride salt (50 mg, 0.20 mM) and triethylamine (28 PL, 0.20 mM) was added and stirring continued at –10° C. for 30 minutes and then for another 30 minutes allowing to warm slowly to room temperature. Ethyl acetate (15 mL) was added and the organic layer washed with aqueous hydrochloric acid (10 mL), saturated sodium bicarbonate solution (15 mL) and dried over magnesium sulphate. After evaporation of solvents in vacuo, the product was obtained as a white solid after purification by preparative thin layer chromatography using 50% petrol/diethyl ether as eluant (33 mg, 39%, mixture of two diastereomers in a ratio of 1:1 and as a mixture of ketone and hydrate in a ratio of 1:4 by $^{19}$F-NMR in d$_6$-acetone): $^1$H NMR (500 MHz, d$_6$-acetone): δ 7.58 (d, br, J=8 Hz, 1H), 6.95–7.40 (m, 4×10H), 4.98–5.15 (m, 4×3H), 4.23 (q, J=7 Hz, 1H), 4.174.29 (m, 2×1H), 4.14 (q, J=7 Hz, 1H), 3.24–3.31 and 2.85–3.01 (m, 4×2H), 1.27 (d, J=7 Hz, 3H), 1.23 (d, J=7 Hz, 3H), 1.18 (d, J=7 Hz, 3H), 1.09 (d, J=7 Hz, 3H); $^{13}$C NMR (125.7 MHz, CDCl$_3$, only the signals for the hydrated form are quoted): δ 175.6, 175.4, 156.7, 139.4, 139.3, 138.1, 130.3, 130.2, 129.3, 129.2, 129.1, 128.6, 127.7, 127.1, 127.0, 122.5 (q, $J_{C-F}$=289 Hz), 94.7–95.8 (m), 66.9, 66.8, 57.5, 56.5, 51.3, 51.1, 34.6, 34.1, 18.3, 18.0; $^{19}$F NMR (235.19 MHz, CDCl$_3$): δ –76.2, –76.3, –82.1, –82.3; m/z (NH$_3$): 423 (MH$^+$); HRMS: calcd for C$_{21}$H$_{22}$F$_3$N$_2$O$_4$ (MH$^+$): 423.1531; found: 423.1531.

N-Fluorenylmethoxycarbonyl-(L)-isoleucinyl-N-[(3S-)-3-(4-phenyl-1,1,1-trifluorobutan-2-one)] amide (25): To a solution of N-fluorenylmethoxycarbonyl-(L)-isoleucine (62 mg, 0.18 mM) and (3S)-3-amino-4-phenyl-1,1,1-trifluorobutan-2-one hydrochloride salt (44 mg, 0.18 mM) in dry DCM (5 mL) was added pyridine (301 μl, 0.36 mM) followed by the formation of a white precipitate. After stirring at room temperature for 1 hour DCM was added (10 mL) and the organic layer washed with aqueous hydrochloric acid (10 mL), saturated sodium bicarbonate solution (15 mL) and brine (10 mL). Drying over magnesium sulphate and evaporation of solvents in vacuo, gave 25 as a pale yellow solid (60 mg, 60%, single diastereomer as a mixture of ketone and hydrate in a ratio of 2:1 by $^{19}$F-NMR in CDCl$_3$): $^1$H NMR (500 MHz, CDCl$_3$): E 7.10–7.70 (m, 13H), 5.31–5.39 (m, 1!H), 5.08–5.12 (m, 1H), 4.45.4.55 (m, 3H), 4.25 (t, J=7 Hz, 1H), 2.25–3.35 (m, 2H), 1.15–1.60 (m, 3H), 0.81–1.10 (m, 6H); $^{19}$F NMR (235.19 MHz, CDCl$_3$): δ −76.2, −82.9; m/z (Scan AP$^+$): 553 (MH$^+$).

REFERENCES

1.) Kitazume, G.; Ishikawa, N. *Chem. Lett.* 1981, 1679–1680.
2.) Ruppert, I.; Schlich, K.; Volbach, W. *Tetrahedron Lett.* 1984, 25, 2195–2198.
3.) Krishnamurti, R.; Bellew, D. R.; Prakash, G. K. S. *J. Org. Chem* 1991, 56, 984–9.
4.) Walter, M. W.; Adlington, R. M.; Baldwin, J. E.; Chuhan, J.; Schofield, C. J. *Tetrahedron Lett.* 1995, 36, 77614.
5.) Ben-Ishai, D. *J. Am. Chem. Soc.* 1957, 79, 5736–5738.
6.) Hiskey, R. G.; Jung, J. M. *J. Am. Chem. Soc.* 1963, 85, 578–582.
7.) Karady, S.; Amato, J. S.; Weinstock, L. M. *Tetrahedron Lett.* 1984, 25, 4337–4340.
8.) Seebach, D.; Fadel, A. *Helv. Chim. Acta* 1985, 68, 1243–1250.
9.) Carpino, L. A.; Sadat-Aalaee, D.; Chao, H. G.; Deselms, H. H. *J. Am. Chem. Soc.* 1990, 112, 9651–9652.
10.) Carpino, L. A.; El-Sayed, M. E. M.; Sadat-Aalaee, D. *J. Am. Chem. Soc.* 1991, 56, 2611–2614.
11.) Scholtz, J. M.; Bartlett, P. A. Synthesis 1989, 542–544.

We claim:

1. An antibacterial formulation comprising a mixture of a β-lactam antibiotic and perfluoro-lower-alkyl derivative of an amino acid having the formula

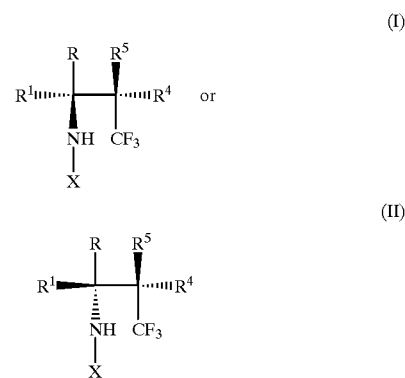

where either $R^4$ is OH and $R^5$ is H or $C_1$–$C_{12}$ hydrocarbon; or $R^5$ is OH and $R^4$ is H or $C_1$–$C_{12}$ hydrocarbon; or each of $R^4$ and $R^5$ is H; or $R^4$ and $R^5$ together are =O, R and $R^1$ are the same or different and each is H or $C_1$–$C_{12}$ hydrocarbon which is either unsubstituted or which carries an acidic or a basic substituent, X is —COR or —COCH$_2$OR or —COOR or a peptide residue, or H; and acid salts thereof.

2. The antibacterial formulation as claimed in claim 1, wherein one of R and $R^1$ is H and the other is $C_1$–$C_{12}$ aromatic or aliphatic hydrocarbon, either one of $R^4$ and $R^5$ is H and the other is OH, or $R^4$ and $R^5$ together are =O and X is —COCH$_2$OR.

3. A method of inhibiting a metallo-β-lactamase enzyme by contacting the enzyme with a perfluoro-lower-alkyl derivative of an amino acid, wherein the perfluoro-lower-alkyl derivative of the amino acid has the formula

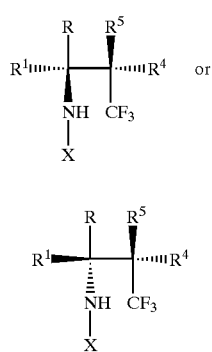

where either $R^4$ is OH and $R^5$ is H or $C_1$–$C_{12}$ hydrocarbon; or $R^5$ is OH and $R^4$ is H or $C_1$–$C_{12}$ hydrocarbon; or each of $R^4$ and $R^5$ is H; or $R^4$ and $R^5$ together are =O, R and $R^1$ are the same or different and each is H or $C_1$–$C_{12}$ hydrocarbon which is either unsubstituted or which carries and acidic or a basic substituent, X is —COR or —COCH$_2$OR or —COOR or a peptide residue, or H; and acid salts thereof.

4. The method of claim 3, wherein one of R and $R^1$ is H and the other is $C_1$–$C_{12}$ aromatic or aliphatic hydrocarbon, either one of $R^4$ and $R^5$ is H and the other is OH or $R^4$ and $R^5$ together are =O and X is —COCH$_2$OR.

5. An antibacterial method which comprises contacting bacteria with a β-lactam antibiotic and with a perfluoro-lower-alkyl derivative of an amino acid, wherein the perfluoro-lower-alkyl derivative of the amino acid has the formula

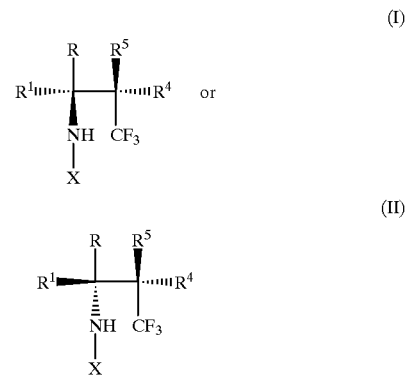

where either $R^4$ is OH and $R^5$ is H or $C_1$–$C_2$ hydrocarbon; or $R^5$ is OH and $R^4$ is H or $C_1$–$C_{12}$ hydrocarbon; or each of $R^4$ and $R^5$ is H; or $R^4$ and $R^5$ together are =O, R and $R^1$ are the same or different and each is H or $C_1$–$C_{12}$ hydrocarbon which is either unsubstituted or which carries and acidic or a basic substituent, X is —COR or —COCH$_2$OR or —COOR or a peptide residue, or H; and acid salts thereof.

6. The antibacterial method of claim 5, wherein one of R and $R^1$ is H and the other is $C_1$–$C_{12}$ aromatic or aliphatic hydrocarbon, either one of $R^4$ and $R^5$ is H and the other is OH or $R^4$ and $R^5$ together are =O and X is —COCH$_2$OR.

* * * * *